United States Patent
Allawi et al.

(10) Patent No.: US 8,190,371 B2
(45) Date of Patent: May 29, 2012

(54) METHODS AND APPLICATIONS FOR TARGET QUANTIFICATION

(75) Inventors: Hatim T. Allawi, Madison, WI (US);
Victor Lyamichev, Madison, WI (US);
Rex Piper, Madison, WI (US)

(73) Assignee: Third Wave Technologies, Inc., Madison, WI (US)

( * ) Notice: Subject to any disclaimer, the term of this patent is extended or adjusted under 35 U.S.C. 154(b) by 396 days.

(21) Appl. No.: 12/206,436

(22) Filed: Sep. 8, 2008
(Under 37 CFR 1.47)

(65) Prior Publication Data

US 2009/0299641 A1  Dec. 3, 2009

Related U.S. Application Data

(60) Provisional application No. 60/970,707, filed on Sep. 7, 2007.

(51) Int. Cl.
*G06F 19/00* (2011.01)
*G06F 17/40* (2006.01)

(52) U.S. Cl. ............... 702/19; 73/432.1; 436/8; 702/20; 702/187; 702/189

(58) Field of Classification Search ............... 73/432.1, 73/865.8, 865.9; 436/2, 8, 815; 702/1, 19, 702/20, 22, 27, 30, 32, 127, 187, 189
See application file for complete search history.

(56) References Cited

U.S. PATENT DOCUMENTS

| | | | |
|---|---|---|---|
| 4,024,742 A * | 5/1977 | Vucich et al. | 72/42 |
| 4,047,890 A * | 9/1977 | Eichelberger et al. | 436/69 |
| 4,607,524 A * | 8/1986 | Gringarten | 73/152.02 |
| 5,011,769 A | 4/1991 | Duck | |
| 5,124,246 A | 6/1992 | Urdea | |
| 5,288,609 A | 2/1994 | Engelhardt | |
| 5,403,711 A | 4/1995 | Walder | |
| 5,409,818 A | 4/1995 | Davey | |
| 5,624,802 A | 4/1997 | Urdea | |
| 5,660,988 A | 8/1997 | Duck | |
| 5,710,264 A | 1/1998 | Urdea | |
| 5,792,614 A | 8/1998 | Western | |
| 5,846,717 A | 12/1998 | Brow | |
| 5,849,481 A | 12/1998 | Urdea | |
| 5,851,770 A | 12/1998 | Babon | |
| 5,882,867 A | 3/1999 | Ullman | |

(Continued)

FOREIGN PATENT DOCUMENTS

WO  9727214  7/1997

(Continued)

OTHER PUBLICATIONS

Swillens et al., "Instant evaluation of the absolute initial number of cDNA copies from a single real-time PCR curve" 2004 Nucleic Acids Research vol. 32(6) e53.

(Continued)

*Primary Examiner* — Edward Cosimano
(74) *Attorney, Agent, or Firm* — Casimir Jones, S.C.

(57) ABSTRACT

The present invention provides methods and software applications for quantifying a target in an experimental sample by collecting and processing initial signal data from the experimental sample and at least two standard control samples containing known target copy numbers. In this regards, the present invention allows the quantification of target copy number in the experimental sample.

12 Claims, 23 Drawing Sheets

U.S. PATENT DOCUMENTS

| | | | |
|---|---|---|---|
| 5,914,230 A | 6/1999 | Liu | |
| 5,958,692 A | 9/1999 | Cotton | |
| 5,985,557 A | 11/1999 | Prudent | |
| 5,994,069 A | 11/1999 | Hall | |
| 6,001,567 A | 12/1999 | Brow | |
| 6,013,170 A | 1/2000 | Meade | |
| 6,063,573 A | 5/2000 | Kayyem | |
| 6,090,543 A | 7/2000 | Prudent | |
| 6,110,677 A | 8/2000 | Western | |
| 6,110,684 A | 8/2000 | Kemper | |
| 6,121,001 A | 9/2000 | Western | |
| 6,150,097 A | 11/2000 | Tyagi | |
| 6,183,960 B1 | 2/2001 | Lizardi | |
| 6,210,884 B1 | 4/2001 | Lizardi | |
| 6,221,583 B1 | 4/2001 | Kayyem | |
| 6,235,502 B1 | 5/2001 | Weissman | |
| 6,248,229 B1 | 6/2001 | Meade | |
| 6,524,861 B1 * | 2/2003 | Anderson | 436/69 |
| 6,898,532 B1 * | 5/2005 | Toh et al. | 702/22 |
| 7,739,054 B2 * | 6/2010 | Carrick et al. | 702/19 |
| 7,831,417 B2 * | 11/2010 | Carrick et al. | 703/2 |
| 2006/0292619 A1 | 12/2006 | Carrick | |
| 2007/0111246 A1 * | 5/2007 | Carrick et al. | 435/6 |
| 2011/0040490 A1 * | 2/2011 | Carrick et al. | 702/19 |

FOREIGN PATENT DOCUMENTS

| | | |
|---|---|---|
| WO | 9842873 | 1/1998 |
| WO | 98/36096 A2 | 8/1998 |
| WO | 2009033156 A3 | 3/2009 |
| WO | 01/66799 A2 | 9/2011 |

OTHER PUBLICATIONS

Jo Vandesompele et al., "Accurate normalization of real-time quantitative RT-PCR data by geometric averaging of multiple internal control genes" 2002 Genome Biology vol. 3(7) research 0034.1-0034.11.

Vaerman et al., "Evaluation of real-time PCR data" 2004 Journal of Biological Regulators and Homeostatic Agents vol. 18, pp. 212-214.

Lyamichev et al., "Polymorphism identification and quantitative detection of genomic DNA by invasive cleavage of oligonucleotide probes" 1999 Nat. Biotech. 17:292.

Hall et al., "Sensitive detection of DNA polymorphisms by the serial invasive signal amplification reaction" 2000 PNAS 97:8272.

Barany, "Genetic disease detection and DNA amplification using cloned thermostable ligase." 1991 PNAS 88, pp. 189-93.

* cited by examiner

| 11 sec/cycle Cycles | Yellow B4 | FAM B4 | Yellow E4 | FAM E4 | Yellow F4 | FAM F4 |
|---|---|---|---|---|---|---|
| 1 | 1 | 0.674 | 1 | 0.576 | 1 | 0.551 |
| 2 | 1 | 0.711 | 1 | 0.576 | 1 | 0.553 |
| 3 | 1 | 0.758 | 1 | 0.577 | 1 | 0.554 |
| 4 | 1 | 0.816 | 1 | 0.579 | 1 | 0.555 |
| 5 | 1 | 0.880 | 1 | 0.581 | 1 | 0.555 |
| 6 | 1 | 0.950 | 1 | 0.583 | 1 | 0.557 |
| 7 | 1 | 1.035 | 1 | 0.586 | 1 | 0.557 |
| 8 | 1 | 1.126 | 1 | 0.589 | 1 | 0.557 |
| 9 | 1 | 1.226 | 1 | 0.592 | 1 | 0.559 |
| 10 | 1 | 1.334 | 1 | 0.596 | 1 | 0.561 |
| 11 | 1 | 1.445 | 1 | 0.600 | 1 | 0.562 |
| 12 | 1 | 1.561 | 1 | 0.606 | 1 | 0.563 |
| 13 | 1 | 1.684 | 1 | 0.610 | 1 | 0.564 |
| 14 | 1 | 1.811 | 1 | 0.616 | 1 | 0.565 |
| 15 | 1 | 1.947 | 1 | 0.625 | 1 | 0.566 |
| 16 | 1 | 2.086 | 1 | 0.633 | 1 | 0.568 |
| 17 | 1 | 2.217 | 1 | 0.638 | 1 | 0.570 |
| 18 | 1 | 2.344 | 1 | 0.645 | 1 | 0.569 |
| 19 | 1 | 2.472 | 1 | 0.653 | 1 | 0.570 |
| 20 | 1 | 2.609 | 1 | 0.660 | 1 | 0.572 |
| 21 | 1 | 2.740 | 1 | 0.668 | 1 | 0.571 |
| 22 | 1 | 2.861 | 1 | 0.677 | 1 | 0.571 |
| 23 | 1 | 2.980 | 1 | 0.688 | 1 | 0.575 |
| 24 | 1 | 3.100 | 1 | 0.697 | 1 | 0.577 |
| 25 | 1 | 3.215 | 1 | 0.705 | 1 | 0.579 |
| 26 | 1 | 3.308 | 1 | 0.715 | 1 | 0.579 |
| 27 | 1 | 3.394 | 1 | 0.724 | 1 | 0.579 |
| 28 | 1 | 3.489 | 1 | 0.734 | 1 | 0.582 |
| 29 | 1 | 3.575 | 1 | 0.748 | 1 | 0.585 |
| 30 | 1 | 3.649 | 1 | 0.762 | 1 | 0.588 |
| 31 | 1 | 3.714 | 1 | 0.772 | 1 | 0.589 |
| 32 | 1 | 3.767 | 1 | 0.782 | 1 | 0.590 |
| 33 | 1 | 3.814 | 1 | 0.795 | 1 | 0.592 |
| 34 | 1 | 3.853 | 1 | 0.809 | 1 | 0.594 |
| 35 | 1 | 3.889 | 1 | 0.824 | 1 | 0.596 |
| 36 | 1 | 3.919 | 1 | 0.837 | 1 | 0.597 |
| 37 | 1 | 3.933 | 1 | 0.851 | 1 | 0.600 |
| 38 | 1 | 3.949 | 1 | 0.866 | 1 | 0.604 |
| 39 | 1 | 3.971 | 1 | 0.883 | 1 | 0.607 |
| 40 | 1 | 3.995 | 1 | 0.898 | 1 | 0.610 |
| 41 | 1 | 4.003 | 1 | 0.910 | 1 | 0.612 |
| 42 | 1 | 4.001 | 1 | 0.924 | 1 | 0.615 |
| 43 | 1 | 4.006 | 1 | 0.938 | 1 | 0.618 |
| 44 | 1 | 4.026 | 1 | 0.951 | 1 | 0.622 |
| 45 | 1 | 4.038 | 1 | 0.969 | 1 | 0.626 |
| 46 | 1 | 4.028 | 1 | 0.989 | 1 | 0.627 |
| 47 | 1 | 4.035 | 1 | 1.004 | 1 | 0.628 |
| 48 | 1 | 4.053 | 1 | 1.019 | 1 | 0.630 |
| 49 | 1 | 4.053 | 1 | 1.036 | 1 | 0.634 |
| 50 | 1 | 4.057 | 1 | 1.053 | 1 | 0.638 |
| 51 | 1 | 4.060 | 1 | 1.069 | 1 | 0.640 |

FIG. 3B

| | | | | | | |
|---|---|---|---|---|---|---|
| 52 | 1 | 4.080 | 1 | 1.090 | 1 | 0.644 |
| 53 | 1 | 4.068 | 1 | 1.110 | 1 | 0.646 |
| 54 | 1 | 4.083 | 1 | 1.127 | 1 | 0.646 |
| 55 | 1 | 4.092 | 1 | 1.146 | 1 | 0.648 |
| 56 | 1 | 4.089 | 1 | 1.167 | 1 | 0.652 |
| 57 | 1 | 4.077 | 1 | 1.183 | 1 | 0.657 |
| 58 | 1 | 4.083 | 1 | 1.200 | 1 | 0.660 |
| 59 | 1 | 4.102 | 1 | 1.219 | 1 | 0.663 |
| 60 | 1 | 4.104 | 1 | 1.238 | 1 | 0.668 |
| 61 | 1 | 4.102 | 1 | 1.256 | 1 | 0.672 |
| 62 | 1 | 4.107 | 1 | 1.278 | 1 | 0.674 |
| 63 | 1 | 4.107 | 1 | 1.300 | 1 | 0.678 |
| 64 | 1 | 4.108 | 1 | 1.319 | 1 | 0.681 |
| 65 | 1 | 4.113 | 1 | 1.340 | 1 | 0.683 |
| 66 | 1 | 4.120 | 1 | 1.362 | 1 | 0.685 |
| 67 | 1 | 4.128 | 1 | 1.383 | 1 | 0.690 |
| 68 | 1 | 4.123 | 1 | 1.408 | 1 | 0.695 |
| 69 | 1 | 4.131 | 1 | 1.430 | 1 | 0.698 |
| 70 | 1 | 4.139 | 1 | 1.452 | 1 | 0.702 |
| 71 | 1 | 4.130 | 1 | 1.476 | 1 | 0.707 |
| 72 | 1 | 4.138 | 1 | 1.494 | 1 | 0.710 |
| 73 | 1 | 4.140 | 1 | 1.514 | 1 | 0.714 |
| 74 | 1 | 4.146 | 1 | 1.536 | 1 | 0.718 |
| 75 | 1 | 4.138 | 1 | 1.560 | 1 | 0.720 |
| 76 | 1 | 4.130 | 1 | 1.577 | 1 | 0.723 |
| 77 | 1 | 4.127 | 1 | 1.601 | 1 | 0.726 |
| 78 | 1 | 4.129 | 1 | 1.623 | 1 | 0.731 |
| 79 | 1 | 4.139 | 1 | 1.648 | 1 | 0.735 |
| 80 | 1 | 4.141 | 1 | 1.677 | 1 | 0.739 |
| 81 | 1 | 4.140 | 1 | 1.699 | 1 | 0.744 |
| 82 | 1 | 4.133 | 1 | 1.719 | 1 | 0.747 |
| 83 | 1 | 4.135 | 1 | 1.746 | 1 | 0.752 |
| 84 | 1 | 4.155 | 1 | 1.771 | 1 | 0.760 |
| 85 | 1 | 4.158 | 1 | 1.792 | 1 | 0.766 |
| 86 | 1 | 4.159 | 1 | 1.815 | 1 | 0.766 |
| 87 | 1 | 4.159 | 1 | 1.839 | 1 | 0.770 |
| 88 | 1 | 4.156 | 1 | 1.857 | 1 | 0.773 |
| 89 | 1 | 4.168 | 1 | 1.875 | 1 | 0.778 |
| 90 | 1 | 4.173 | 1 | 1.899 | 1 | 0.784 |
| 91 | 1 | 4.167 | 1 | 1.921 | 1 | 0.786 |
| 92 | 1 | 4.165 | 1 | 1.943 | 1 | 0.789 |
| 93 | 1 | 4.166 | 1 | 1.966 | 1 | 0.795 |
| 94 | 1 | 4.160 | 1 | 1.994 | 1 | 0.802 |
| 95 | 1 | 4.157 | 1 | 2.019 | 1 | 0.807 |
| 96 | 1 | 4.159 | 1 | 2.040 | 1 | 0.809 |
| 97 | 1 | 4.156 | 1 | 2.063 | 1 | 0.813 |
| 98 | 1 | 4.151 | 1 | 2.090 | 1 | 0.818 |
| 99 | 1 | 4.154 | 1 | 2.118 | 1 | 0.825 |
| 100 | 1 | 4.173 | 1 | 2.144 | 1 | 0.831 |
| 101 | 1 | 4.184 | 1 | 2.173 | 1 | 0.834 |
| 102 | 1 | 4.182 | 1 | 2.195 | 1 | 0.837 |
| 103 | 1 | 4.182 | 1 | 2.213 | 1 | 0.843 |
| 104 | 1 | 4.176 | 1 | 2.244 | 1 | 0.850 |
| 105 | 1 | 4.178 | 1 | 2.276 | 1 | 0.855 |
| 106 | 1 | 4.186 | 1 | 2.290 | 1 | 0.857 |

FIG. 3C

| | | | | | | |
|---|---|---|---|---|---|---|
| 107 | 1 | 4.176 | 1 | 2.308 | 1 | 0.859 |
| 108 | 1 | 4.167 | 1 | 2.341 | 1 | 0.863 |
| 109 | 1 | 4.169 | 1 | 2.373 | 1 | 0.869 |
| 110 | 1 | 4.169 | 1 | 2.396 | 1 | 0.876 |
| 111 | 1 | 4.183 | 1 | 2.416 | 1 | 0.881 |
| 112 | 1 | 4.194 | 1 | 2.439 | 1 | 0.885 |
| 113 | 1 | 4.188 | 1 | 2.463 | 1 | 0.888 |
| 114 | 1 | 4.184 | 1 | 2.487 | 1 | 0.893 |
| 115 | 1 | 4.185 | 1 | 2.509 | 1 | 0.900 |
| 116 | 1 | 4.188 | 1 | 2.531 | 1 | 0.905 |
| 117 | 1 | 4.193 | 1 | 2.542 | 1 | 0.910 |
| 118 | 1 | 4.196 | 1 | 2.555 | 1 | 0.916 |
| 119 | 1 | 4.197 | 1 | 2.583 | 1 | 0.921 |
| 120 | 1 | 4.194 | 1 | 2.626 | 1 | 0.927 |
| 121 | 1 | 4.199 | 1 | 2.652 | 1 | 0.933 |
| 122 | 1 | 4.194 | 1 | 2.677 | 1 | 0.938 |
| 123 | 1 | 4.188 | 1 | 2.702 | 1 | 0.945 |
| 124 | 1 | 4.189 | 1 | 2.728 | 1 | 0.950 |
| 125 | 1 | 4.196 | 1 | 2.741 | 1 | 0.954 |
| 126 | 1 | 4.198 | 1 | 2.757 | 1 | 0.960 |
| 127 | 1 | 4.193 | 1 | 2.776 | 1 | 0.964 |
| 128 | 1 | 4.205 | 1 | 2.793 | 1 | 0.969 |
| 129 | 1 | 4.202 | 1 | 2.823 | 1 | 0.975 |
| 130 | 1 | 4.203 | 1 | 2.857 | 1 | 0.981 |
| 131 | 1 | 4.219 | 1 | 2.888 | 1 | 0.988 |
| 132 | 1 | 4.219 | 1 | 2.919 | 1 | 0.995 |
| 133 | 1 | 4.216 | 1 | 2.930 | 1 | 0.998 |
| 134 | 1 | 4.218 | 1 | 2.934 | 1 | 1.000 |
| 135 | 1 | 4.219 | 1 | 2.957 | 1 | 1.006 |
| 136 | 1 | 4.219 | 1 | 2.986 | 1 | 1.012 |
| 137 | 1 | 4.210 | 1 | 3.011 | 1 | 1.018 |
| 138 | 1 | 4.193 | 1 | 3.031 | 1 | 1.022 |
| 139 | 1 | 4.195 | 1 | 3.050 | 1 | 1.028 |
| 140 | 1 | 4.205 | 1 | 3.068 | 1 | 1.033 |
| 141 | 1 | 4.204 | 1 | 3.086 | 1 | 1.041 |
| 142 | 1 | 4.210 | 1 | 3.117 | 1 | 1.046 |
| 143 | 1 | 4.221 | 1 | 3.134 | 1 | 1.050 |
| 144 | 1 | 4.234 | 1 | 3.159 | 1 | 1.058 |
| 145 | 1 | 4.249 | 1 | 3.182 | 1 | 1.068 |
| 146 | 1 | 4.251 | 1 | 3.201 | 1 | 1.077 |
| 147 | 1 | 4.237 | 1 | 3.216 | 1 | 1.079 |
| 148 | 1 | 4.233 | 1 | 3.238 | 1 | 1.082 |
| 149 | 1 | 4.240 | 1 | 3.263 | 1 | 1.087 |
| 150 | 1 | 4.240 | 1 | 3.290 | 1 | 1.093 |
| 151 | 1 | 4.232 | 1 | 3.309 | 1 | 1.099 |
| 152 | 1 | 4.219 | 1 | 3.319 | 1 | 1.105 |
| 153 | 1 | 4.218 | 1 | 3.346 | 1 | 1.113 |
| 154 | 1 | 4.226 | 1 | 3.372 | 1 | 1.120 |
| 155 | 1 | 4.232 | 1 | 3.385 | 1 | 1.125 |
| 156 | 1 | 4.228 | 1 | 3.397 | 1 | 1.127 |
| 157 | 1 | 4.226 | 1 | 3.404 | 1 | 1.130 |
| 158 | 1 | 4.236 | 1 | 3.424 | 1 | 1.135 |
| 159 | 1 | 4.241 | 1 | 3.459 | 1 | 1.143 |
| 160 | 1 | 4.240 | 1 | 3.481 | 1 | 1.150 |
| 161 | 1 | 4.237 | 1 | 3.500 | 1 | 1.154 |

FIG. 3D

| | | | | | | |
|---|---|---|---|---|---|---|
| 162 | 1 | 4.235 | 1 | 3.522 | 1 | 1.161 |
| 163 | 1 | 4.241 | 1 | 3.541 | 1 | 1.168 |
| 164 | 1 | 4.251 | 1 | 3.563 | 1 | 1.171 |
| 165 | 1 | 4.265 | 1 | 3.582 | 1 | 1.176 |
| 166 | 1 | 4.273 | 1 | 3.595 | 1 | 1.182 |
| 167 | 1 | 4.265 | 1 | 3.615 | 1 | 1.190 |
| 168 | 1 | 4.247 | 1 | 3.626 | 1 | 1.198 |
| 169 | 1 | 4.255 | 1 | 3.642 | 1 | 1.204 |
| 170 | 1 | 4.270 | 1 | 3.663 | 1 | 1.208 |
| 171 | 1 | 4.255 | 1 | 3.676 | 1 | 1.214 |
| 172 | 1 | 4.242 | 1 | 3.685 | 1 | 1.220 |
| 173 | 1 | 4.247 | 1 | 3.686 | 1 | 1.228 |
| 174 | 1 | 4.253 | 1 | 3.697 | 1 | 1.237 |
| 175 | 1 | 4.257 | 1 | 3.711 | 1 | 1.242 |
| 176 | 1 | 4.252 | 1 | 3.725 | 1 | 1.244 |
| 177 | 1 | 4.244 | 1 | 3.750 | 1 | 1.251 |
| 178 | 1 | 4.252 | 1 | 3.768 | 1 | 1.260 |
| 179 | 1 | 4.269 | 1 | 3.784 | 1 | 1.269 |
| 180 | 1 | 4.267 | 1 | 3.810 | 1 | 1.277 |
| 181 | 1 | 4.264 | 1 | 3.821 | 1 | 1.283 |
| 182 | 1 | 4.271 | 1 | 3.828 | 1 | 1.288 |
| 183 | 1 | 4.274 | 1 | 3.842 | 1 | 1.287 |
| 184 | 1 | 4.278 | 1 | 3.857 | 1 | 1.296 |
| 185 | 1 | 4.284 | 1 | 3.869 | 1 | 1.307 |
| 186 | 1 | 4.282 | 1 | 3.878 | 1 | 1.311 |
| 187 | 1 | 4.281 | 1 | 3.885 | 1 | 1.316 |
| 188 | 1 | 4.281 | 1 | 3.890 | 1 | 1.321 |
| 189 | 1 | 4.280 | 1 | 3.904 | 1 | 1.324 |
| 190 | 1 | 4.273 | 1 | 3.918 | 1 | 1.332 |
| 191 | 1 | 4.269 | 1 | 3.928 | 1 | 1.338 |
| 192 | 1 | 4.275 | 1 | 3.932 | 1 | 1.345 |
| 193 | 1 | 4.274 | 1 | 3.937 | 1 | 1.352 |
| 194 | 1 | 4.274 | 1 | 3.949 | 1 | 1.359 |
| 195 | 1 | 4.287 | 1 | 3.952 | 1 | 1.364 |
| 196 | 1 | 4.283 | 1 | 3.964 | 1 | 1.368 |
| 197 | 1 | 4.284 | 1 | 3.973 | 1 | 1.377 |
| 198 | 1 | 4.275 | 1 | 3.989 | 1 | 1.385 |
| 199 | 1 | 4.276 | 1 | 3.984 | 1 | 1.394 |
| 200 | 1 | 4.290 | 1 | 4.012 | 1 | 1.401 |
| 201 | 1 | 4.303 | 1 | 4.022 | 1 | 1.403 |
| 202 | 1 | 4.295 | 1 | 4.015 | 1 | 1.411 |
| 203 | 1 | 4.281 | 1 | 4.021 | 1 | 1.422 |
| 204 | 1 | 4.288 | 1 | 4.051 | 1 | 1.427 |
| 205 | 1 | 4.301 | 1 | 4.064 | 1 | 1.429 |
| 206 | 1 | 4.301 | 1 | 4.054 | 1 | 1.434 |
| 207 | 1 | 4.293 | 1 | 4.060 | 1 | 1.438 |
| 208 | 1 | 4.296 | 1 | 4.074 | 1 | 1.444 |
| 209 | 1 | 4.298 | 1 | 4.077 | 1 | 1.454 |
| 210 | 1 | 4.292 | 1 | 4.078 | 1 | 1.461 |
| 211 | 1 | 4.294 | 1 | 4.084 | 1 | 1.466 |
| 212 | 1 | 4.286 | 1 | 4.091 | 1 | 1.472 |
| 213 | 1 | 4.280 | 1 | 4.097 | 1 | 1.479 |
| 214 | 1 | 4.280 | 1 | 4.110 | 1 | 1.489 |
| 215 | 1 | 4.272 | 1 | 4.129 | 1 | 1.498 |
| 216 | 1 | 4.278 | 1 | 4.136 | 1 | 1.508 |

FIG. 3E

| 217 | 1 | 4.276 | 1 | 4.145 | 1 | 1.514 |
|---|---|---|---|---|---|---|
| 218 | 1 | 4.280 | 1 | 4.156 | 1 | 1.517 |
| 219 | 1 | 4.302 | 1 | 4.159 | 1 | 1.523 |
| 220 | 1 | 4.312 | 1 | 4.160 | 1 | 1.529 |
| 221 | 1 | 4.305 | 1 | 4.165 | 1 | 1.535 |
| 222 | 1 | 4.290 | 1 | 4.176 | 1 | 1.542 |
| 223 | 1 | 4.288 | 1 | 4.185 | 1 | 1.546 |
| 224 | 1 | 4.300 | 1 | 4.104 | 1 | 1.553 |
| 225 | 1 | 4.294 | 1 | 4.178 | 1 | 1.566 |
| 226 | 1 | 4.288 | 1 | 4.182 | 1 | 1.572 |
| 227 | 1 | 4.300 | 1 | 4.183 | 1 | 1.578 |
| 228 | 1 | 4.304 | 1 | 4.187 | 1 | 1.587 |
| 229 | 1 | 4.297 | 1 | 4.207 | 1 | 1.594 |
| 230 | 1 | 4.295 | 1 | 4.207 | 1 | 1.599 |
| 231 | 1 | 4.300 | 1 | 4.210 | 1 | 1.606 |
| 232 | 1 | 4.302 | 1 | 4.229 | 1 | 1.609 |
| 233 | 1 | 4.310 | 1 | 4.230 | 1 | 1.612 |
| 234 | 1 | 4.314 | 1 | 4.219 | 1 | 1.623 |
| 235 | 1 | 4.303 | 1 | 4.221 | 1 | 1.629 |
| 236 | 1 | 4.301 | 1 | 4.224 | 1 | 1.634 |
| 237 | 1 | 4.305 | 1 | 4.221 | 1 | 1.642 |
| 238 | 1 | 4.296 | 1 | 4.233 | 1 | 1.648 |
| 239 | 1 | 4.291 | 1 | 4.250 | 1 | 1.653 |
| 240 | 1 | 4.302 | 1 | 4.249 | 1 | 1.655 |
| 241 | 1 | 4.307 | 1 | 4.252 | 1 | 1.657 |
| 242 | 1 | 4.310 | 1 | 4.250 | 1 | 1.667 |
| 243 | 1 | 4.309 | 1 | 4.256 | 1 | 1.675 |
| 244 | 1 | 4.297 | 1 | 4.271 | 1 | 1.683 |
| 245 | 1 | 4.295 | 1 | 4.266 | 1 | 1.692 |
| 246 | 1 | 4.299 | 1 | 4.266 | 1 | 1.699 |
| 247 | 1 | 4.310 | 1 | 4.269 | 1 | 1.703 |
| 248 | 1 | 4.324 | 1 | 4.270 | 1 | 1.712 |
| 249 | 1 | 4.330 | 1 | 4.273 | 1 | 1.725 |

FIG. 4
A. Standard Control Curves
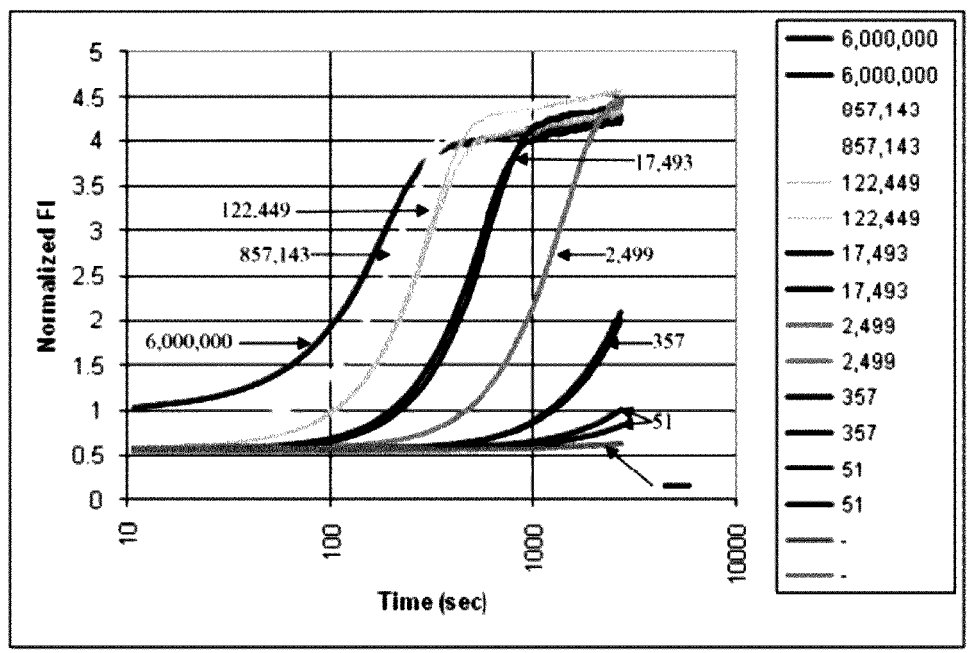
B. Experimental Curves
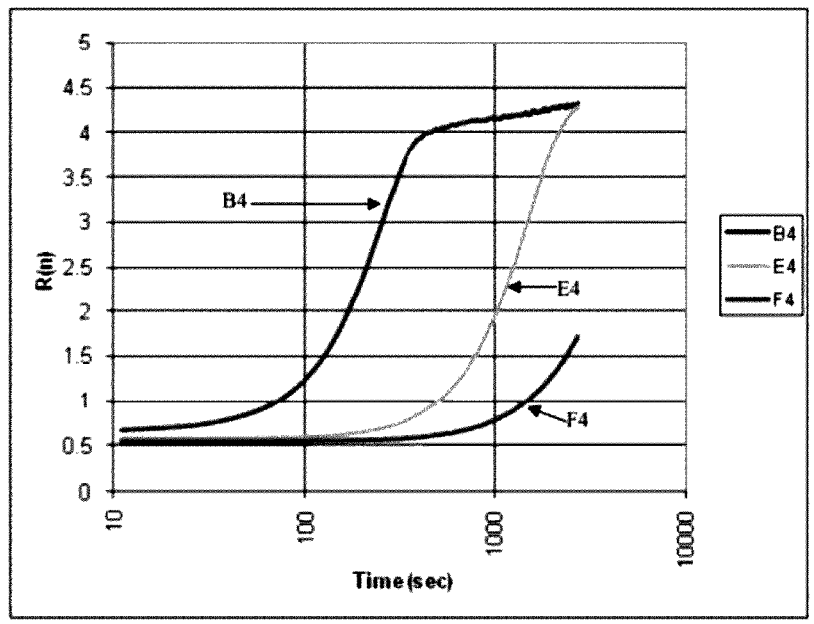

FIG. 5
A. Standard Control Curves with Added Threshold
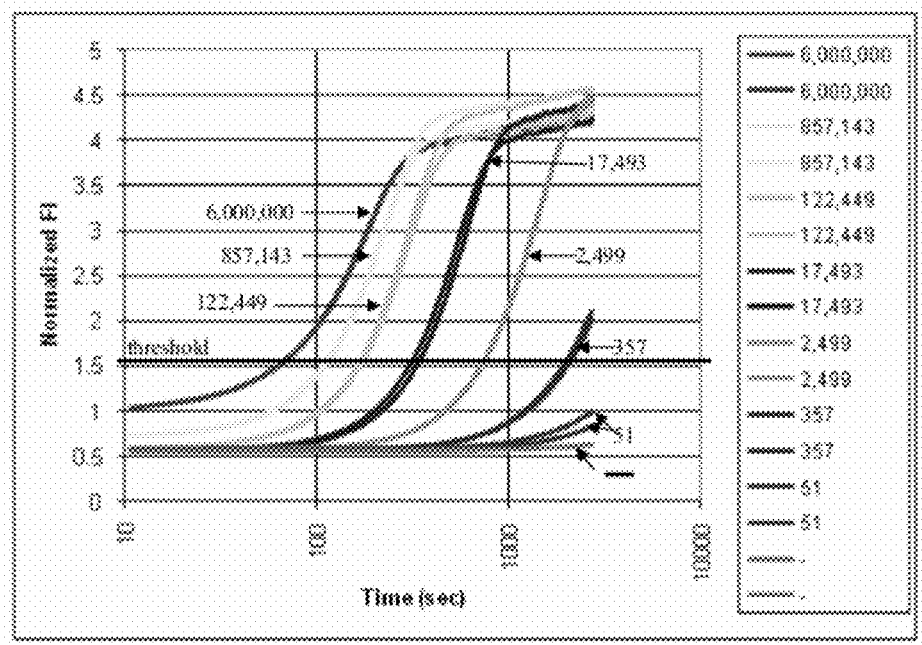
B. Experimental Curves with Added Threshold
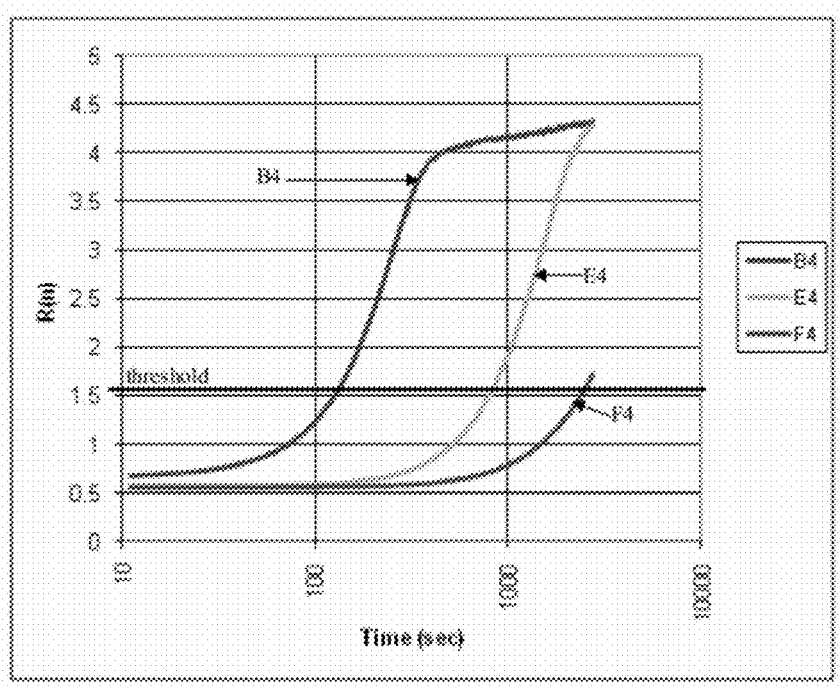

METHODS AND APPLICATIONS FOR TARGET QUANTIFICATION

The present application claims priority to expired U.S. Provisional Application Ser. No. 60/970,707, filed Sep. 7, 2007, which is herein incorporated by reference in its entirety.

FIELD OF THE INVENTION

The present invention relates to methods and software applications for quantifying a target in an experimental sample. Preferably, the target is a nucleic acid sequence which is detected by a nucleic acid detection assay.

BACKGROUND OF THE INVENTION

The quantification of nucleic acids plays an important role in the fields of biology and medicine. For example, quantification of nucleic acid is important in cancer diagnosis and prognosis and viral diagnosis and judgments of therapeutic effects (e.g., for HCV and HIV). HCV RNA quantification is important for patients taking IFN. The effect of IFN therapy can be directly found by monitoring the amount of virus during IFN therapy. This enables more effective IFN therapy that is tailored to clinical conditions of each patient. Quantification of target nucleic acid is important for diagnosis of diseases in the future. For example, earlier diagnosis can be effected by examining the expression level of mRNA that responds to exogenous stimuli in the case of a disease that results from exogenous stimuli.

The polymerase chain reaction can be employed for nucleic acid quantification. However, when PCR is employed, the absolute amount of the amplified nucleic acids does not accurately reflect the amount of the target nucleic acid that had existed when amplification was initiated. At first, the amount of the product amplified by PCR generally exponentially increases every cycle, however, the rate of increase slows down and then stops when the amount of the amplified product exceeds a certain level. Thus, the final amount of the amplified product is constant regardless of the amount of the target nucleic acid when the reaction was initiated. This phenomenon is referred to as the plateau effect, which should be taken into consideration when quantifying the product amplified by PCR.

A technique known as real time PCR is widely employed for target sequence quantification. In this technique, a serial dilution of the target nucleic acid is prepared, each sample is subjected to PCR, and the time course is then taken in real time. The threshold cycle (the Ct value), with which a given amount of amplified product is obtained in a region where amplification exponentially occurs before reaching the level of the plateau effect, is determined. The determined value is plotted on a vertical axis, and the amount of nucleic acid is plotted on a horizontal axis. Thus, a calibration curve is prepared. An unknown sample of interest is subjected to PCR under the same conditions and the Ct value is determined. This enables the quantification of the amount of nucleic acid in the unknown sample. A device for real time detection is generally expensive. If this technique is performed using a common commercial thermal cycler, the sample has to be analyzed each cycle in order to determine the threshold cycle with which a given amount of amplified product is generated. Thus, this technique requires a large amount of labor.

Quantitative competitive PCR is also a widely employed technique. In this technique, a competitor nucleic acid having a sequence similar to that of the target nucleic acid is diluted in a stepwise manner, and the resultants are added to a sample containing the target nucleic acid to be quantified. Depending on the amount of the competitor nucleic acid added, the ratio of the amount of the amplified product from the target nucleic acid to the amount of the amplified product from competitor nucleic acid added, is determined. Accordingly, the point where the amount of the amplified product from target nucleic acid which was added becomes equal to the amount of the amplified product from competitor nucleic acid, represents the amount of the target nucleic acid. Although this technique is relatively simple, the necessity of preparing competitors for each primer complicates the operation. In addition, there is a problem that the amplification efficiency of the target nucleic acid may differ from that of the competitor nucleic acid.

In light of the above, what is needed are relatively simple and inexpensive methods for quantitating nucleic acids, and other targets, in a sample.

SUMMARY OF THE INVENTION

The present invention provides methods and software applications for quantifying a target in an experimental sample by collecting and processing initial signal data from the experimental sample and at least two standard control samples containing known target copy numbers. In particular embodiments, the initial signal data is capable of being plotted as an experimental curve (e.g., sigmoidal curve or other curve) and at least two standard control curves (e.g., sigmoidal curves or other curves). In certain embodiments, the initial signal data is processed with a threshold signal line to generate control and experimental intersecting time values that can be further processed to generate log plot data comprising coordinates for a log/log plot, or linear/log plot. In some embodiments, the log plot data may be processed to generate a slope equation that can be used with the experimental time value to quantify target copy number in the experimental sample.

In some embodiments, the present invention provides methods of quantifying a target in an experimental sample comprising: a) providing: i) initial signal data comprising assay signal level detected at a plurality of time intervals from an experimental sample and at least two standard control samples containing known target copy numbers that are different, wherein the initial signal data is capable of being plotted as an experimental curve and at least two standard control curves; and ii) a threshold signal line having i) an initial signal value at time zero, and ii) a threshold slope; wherein the threshold signal line is above background level and intersects the experimental curve and two or more of the at least two standard control curves; and b) processing the initial signal data and the threshold signal line to generate an experimental intersecting time value and at least two standard control intersecting time values; c) processing the at least two standard control intersecting time values and the known target copy numbers to generate log plot data comprising coordinates for a log/log plot, or linear/log plot, of the intersecting time values versus the known target copy numbers; d) processing the log plot data to generate a slope equation describing a resulting slope fit to the log plot data; and e) processing the experimental intersecting time value with the slope equation to generate a quantified target copy number for the experimental sample.

In other embodiments, the present invention provides methods of quantifying a target in an experimental sample comprising: a) providing; i) a user interface configured to receive initial signal data, and ii) a computer system having stored therein a target quantifying software application, and b) transmitting the initial signal data from the user interface to the computer system, wherein the initial signal data comprises assay signal level detected at a plurality of time intervals from an experimental sample and at least two standard control samples containing known target copy numbers that are different, wherein the signal data is capable of being plotted as an experimental curve and at least two standard control curves; c) processing the signal data with the target quantifying software application such that the target quantifying software: i) generates a threshold signal line having i) an initial signal value at time zero, and ii) a threshold slope; wherein the threshold signal line is above background level and intersects the experimental curve and two or more of the at least two standard control curves; ii) processes the signal data and the threshold signal line to generate an experimental intersecting time value and at least two standard control intersecting time values; iii) processes the at least two standard control intersecting time values and the known target copy numbers to generate log plot data comprising coordinates for a log/log plot, or a linear/log plot, of the intersecting time values versus the known target copy numbers; iv) processes the log plot data to generate a slope equation describing a resulting slope fit to the log plot data; and v) processes the experimental intersecting time value with the slope equation to generate a quantified target copy number for the experimental sample.

In further embodiments, the present invention provides systems for quantifying a target in an experimental sample comprising: a) a device configured to detect assay signal level at a plurality of time intervals from an experimental sample and at least two standard control samples containing known target copy numbers that are different, to generate initial signal data; b) a target quantifying software application configured to: i) process the initial signal data to generate signal data that is capable of being plotted as an experimental curve and at least two standard control curves; ii) generate a threshold signal line having i) an initial signal value at time zero, and ii) a threshold slope; wherein the threshold signal line is above background, and intersects the experimental curve and two or more of the at least two standard control curves; iii) process the signal data and the threshold signal line to generate an experimental intersecting time value and at least two standard control intersecting time values; iv) process the at least two standard control intersecting time values and the known target copy numbers to generate log plot data comprising coordinates for a log/log plot, or linear/log plot, of the intersecting time values versus the known target copy numbers; v) process the log plot data to generate a slope equation describing a resulting slope fit to the log plot data; and vi) process the experimental intersecting time value with the slope equation to generate a quantified target copy number for the experimental sample; and c) a computer system having stored therein the target quantifying software application, wherein the computer system comprises computer memory and a computer processor.

In particular embodiments, the present invention provides computer memory device having stored therein a target quantifying software application, wherein the target quantifying software application is configured to: a) process initial signal data to generate signal data that is capable of being plotted as an experimental curve and at least two standard control curves, wherein the initial signal data comprises assay signal level detected at a plurality of time intervals from an experimental sample and at least two standard control samples containing known target copy numbers that are different; b) generate a threshold signal line having i) an initial signal value at time zero, and ii) a threshold slope; wherein the threshold signal line is above background and intersects the experimental curve and two or more of the at least two standard control curves; c) process the signal data and the threshold signal line to generate an experimental intersecting time value and at least two standard control intersecting time values; d) process the at least two standard control intersecting time values and the known target copy numbers to generate log plot data comprising coordinates for a log/log plot, or linear/log plot, of the intersecting time values versus the known target copy numbers; e) process the log plot data to generate a slope equation describing a resulting slope fit to the log plot data; and f) process the experimental intersecting time value with the slope equation to generate a quantified target copy number for the experimental sample.

In certain embodiments, the present invention provides methods of quantifying a target in an experimental sample, comprising: a) exposing an experimental sample and at least two standard control samples to a nucleic acid detection assay, wherein the at least two standard control samples contain known target copy numbers that are different; b) detecting assay signal levels from: i) the experimental sample, ii) the at least two standard control samples, and iii) at least two internal dye control samples, wherein the assay signal levels are detected at the plurality of time intervals to generate raw signal data; c) normalizing the raw signal data to generate: i) normalized experimental signal data, ii) normalized standard control signal data; and iii) a normalized internal dye control signal value; d) processing the normalized experimental signal data and the normalized standard control signal data to generate signal data that is capable of being plotted as an experimental curve and at least two standard control curves; e) determining at least one threshold signal line having an initial signal value at time zero and a threshold slope, wherein the threshold signal line is: i) above the normalized internal dye control value; ii) intersects the experimental curve; and iii) intersects two or more of the at least two standard control curves; f) processing the signal data and the threshold signal line to generate an experimental intersecting time value and at least two standard control intersecting time values; g) processing the at least two standard control intersecting time values and the known target copy numbers to generate log plot data comprising coordinates for a log/log plot, or linear/log plot, of the intersecting time values versus the known target copy numbers; h) processing the log plot data to generate a slope equation describing a resulting slope fit to the log plot data; and i) processing the experimental intersecting time value with the slope equation to generate a quantified target copy number for the experimental sample.

In other embodiments, the present invention provides methods of quantifying a target in an experimental sample comprising: a) providing: i) initial signal data comprising assay signal level detected at a plurality of time intervals from an experimental sample and at least two standard control samples containing known target copy numbers that are different, wherein the initial signal data is capable of being plotted as an experimental curve and at least two standard control curves; and ii) a plurality of different threshold signal lines each having i) an initial signal value at time zero, and ii) a threshold slope; wherein each of the threshold signal lines are above background level and intersects the experimental curve and two or more of the at least two standard control curves; b) processing the initial signal data and the plurality of threshold signal lines to generate an experimental intersecting time values standard control intersecting time values for each of the different threshold signal lines; c) processing the standard control intersecting time values and the known target copy numbers to generate log plot data for each of the plurality of different threshold signal lines, wherein the log plot data comprises coordinates for a log/log plot, or linear/log plot, of the intersecting time values versus the known target copy numbers; d) processing the log plot data to generate a plurality of slope equations describing a plurality of resulting slopes fit to the log plot data, wherein each of the plurality of resulting slopes has a fit value (e.g., an $R^2$ value); and e) processing the experimental intersecting time values with at least one of the plurality of slope equations to generate a quantified target copy number for the experimental sample.

In particular embodiments, the present invention provides methods of quantifying a target in an experimental sample comprising: a) providing; i) a user interface configured to receive initial signal data, and ii) a computer system having stored therein a target quantifying software application, and b) transmitting the initial signal data from the user interface to the computer system, wherein the initial signal data comprises assay signal level detected at a plurality of time intervals from an experimental sample and at least two standard control samples containing known target copy numbers that are different, wherein the signal data is capable of being plotted as an experimental curve and at least two standard control curves; c) processing the signal data with the target quantifying software application such that the target quantifying software: i) generates a plurality of different threshold signal lines each having i) an initial signal value at time zero, and ii) a threshold slope; wherein each of the threshold signal lines are above background level and intersect the experimental curve and two or more of the at least two standard control curves; ii) processes the signal data and the plurality of threshold signal lines to generate experimental intersecting time values and standard control intersecting time values for each of the different threshold signal lines; iii) processes the standard control intersecting time values and the known target copy numbers to generate log plot data for each of the plurality of different threshold signal lines, wherein the log plot data comprises coordinates for a log/log plot, or a linear/log plot, of the intersecting time values versus the known target copy numbers; iv) processes the log plot data to generate a plurality of slope equations describing a plurality of resulting slopes fit to the log plot data, wherein each of the plurality of resulting slopes has a fit value (e.g., an $R^2$ value); and v) processes the experimental intersecting time values with at least one of the plurality of slope equations to generate a quantified target copy number for the experimental sample.

In some embodiments, the present invention provides systems for quantifying a target in an experimental sample comprising: a) a device configured to detect assay signal level at a plurality of time intervals from an experimental sample and at least two standard control samples containing known target copy numbers that are different, to generate initial signal data; b) a target quantifying software application configured to: i) process the initial signal data to generate signal data that is capable of being plotted as an experimental curve and at least two standard control curves; ii) generate a plurality of different threshold signal lines each having i) an initial signal value at time zero, and ii) a threshold slope; wherein each of the threshold signal lines are above background, and intersects the experimental curve and two or more of the at least two standard control curves; iii) process the signal data and the plurality of threshold signal lines to generate experimental intersecting time values and standard control intersecting time values for each of the different threshold signal lines; iv) process the standard control intersecting time values and the known target copy numbers to generate log plot data for each of the plurality of different threshold signal lines, wherein the log plot data comprises coordinates for a log/log plot, or linear/log plot, of the intersecting time values versus the known target copy numbers; v) process the log plot data to generate a plurality of slope equations describing a plurality of resulting slopes fit to the log plot data, wherein each of the plurality of resulting slopes has a fit value (e.g., an $R^2$ value); and vi) process the experimental intersecting time value with at least one of the plurality of the slope equations to generate a quantified target copy number for the experimental sample; and c) a computer system having stored therein the target quantifying software application, wherein the computer system comprises computer memory and a computer processor.

In other embodiments, the present invention provides computer memory devices having stored therein a target quantifying software application, wherein the target quantifying software application is configured to: a) process initial signal data to generate signal data that is capable of being plotted as an experimental curve and at least two standard control curves, wherein the initial signal data comprises assay signal level detected at a plurality of time intervals from an experimental sample and at least two standard control samples containing known target copy numbers that are different; b) generates a plurality of different threshold signal lines each having i) an initial signal value at time zero, and ii) a threshold slope; wherein each of the threshold signal lines are above background and intersects the experimental curve and two or more of the at least two standard control curves; c) process the signal data and the plurality of threshold signal lines to generate experimental intersecting time values and standard control intersecting time values for each of the different threshold signal lines; d) process the standard control intersecting time values and the known target copy numbers to generate log plot data for each of the plurality of different threshold signal lines, wherein the log plot data comprises coordinates for a log/log plot, or linear/log plot, of the intersecting time values versus the known target copy numbers; e) process the log plot data to generate a plurality of slope equations describing a plurality of resulting slope fit to the log plot data, wherein each of the plurality of resulting slopes has a fit value (e.g., an $R^2$ value); and f) process the experimental intersecting time value with at least one of the plurality of slope equations to generate a quantified target copy number for the experimental sample.

In certain embodiments, the present invention provides methods of quantifying a target in an experimental sample, comprising: a) exposing an experimental sample and at least two standard control samples to a nucleic acid detection assay, wherein the at least two standard control samples contain known target copy numbers that are different; b) detecting assay signal levels from: i) the experimental sample, ii) the at least two standard control samples, and iii) at least two internal dye control samples, wherein the assay signal levels are detected at the plurality of time intervals to generate raw signal data; c) normalizing the raw signal data to generate: i) normalized experimental signal data, ii) normalized standard control signal data; and iii) a normalized internal dye control signal value; d) processing the normalized experimental signal data and the normalized standard control signal data to generate signal data that is capable of being plotted as an experimental curve and at least two standard control curves; e) determining a plurality of threshold signal lines each having an initial signal value at time zero and a threshold slope, wherein each of the threshold signal lines are: i) above the normalized internal dye control value; ii) intersects the experimental curve; and iii) intersects two or more of the at least two standard control curves; f) processing the signal data and the plurality of threshold signal lines to generate an experimental intersecting time value and standard control intersecting time values for each of the different threshold signal lines; g) processing the standard control intersecting time values and the known target copy numbers to generate log plot data for each of the plurality of different threshold signal lines, wherein the log plot data comprises coordinates for a log/log plot, or linear/log plot, of the intersecting time values versus the known target copy numbers; h) processing the log plot data to generate a plurality of slope equation describing a plurality of resulting slope fit to the log plot data, wherein each of the plurality of resulting slopes has a fit value (e.g., an $R^2$ value); and i) processing the experimental intersecting time value with at least one of the plurality of slope equations to generate a quantified target copy number for the experimental sample.

In some embodiments, the at least one slope equation has the best fit value of any of the plurality of resulting slopes. In other embodiments, the plurality of different threshold signal lines is at least two different threshold signal lines (e.g., at least 2, 3, 4 . . . 10 . . . 15 . . . 25 . . . 100 . . . 1000 . . . 10,000 . . . all the possible threshold signal lines that could be generated by a computer).

In certain embodiments, the threshold slope is zero (horizontal line). In further embodiments, the threshold slope is negative (downward sloping line). In particular embodiments, the threshold slope is positive (upward sloping line).

In particular embodiments, the quantified target copy number in the experimental sample is generated within about 150 seconds or less from the time when an assay signal level is first detected from the experimental sample (e.g., within about 75 seconds . . . about 100 seconds . . . about 125 seconds . . . or about 150 seconds). In some embodiments, the quantified target copy number in the experimental sample is generated within about 45 minutes or less from the time when an assay signal level is first detected from the experimental sample (e.g., within about 5 minutes . . . about 15 minutes . . . about 30 minutes . . . or about 45 minutes). In certain embodiments, the quantified target copy number in the experimental sample is generated between about 2 minutes and about 35 minutes from the time when an assay signal is first detected from the experimental sample.

In some embodiments, the assay signal level is generated by a nucleic acid detection assay. In other embodiments, the nucleic acid detection assay comprises an invasive cleavage assay. In further embodiments, the nucleic acid detection assay is performed, or configured to perform, under isothermal conditions. In particular embodiments, the target comprises a nucleic acid sequence. In additional embodiments, the nucleic acid sequence comprises an RNA or DNA sequence. In other embodiments, the nucleic acid sequence comprises a micro-RNA or siRNA sequence. In some embodiments, the assay signal level is generated by a protein, carbohydrate, or small-molecule detection assay (e.g., capable of generating data over time that can be plotted to a curve).

In certain embodiments, the plurality of time intervals are regularly spaced time intervals (e.g., every second . . . every 5 seconds . . . every 30 seconds . . . every minute . . . every 5 minutes). In other embodiments, the plurality of time intervals comprises at least 5 time intervals (e.g., at least 7 . . . 15 . . . 25 . . . 50 . . . 100 . . . 200 . . . 400 . . . 600 . . . 800 . . . 1000 . . . 5000 time intervals). In particular embodiments, the timer intervals are every 5 to 30 seconds.

In some embodiments, the amount of the target in the experimental sample is unknown. In particular embodiments, the at least two standard control samples contain known target copy numbers that differ from each other by a factor of at least about ten (e.g., they differ by 10-fold . . . 15-fold . . . 20-fold . . . 50-fold . . . 100-fold . . . or more). In other embodiments, the at least two standard control samples comprise 2 to 100 standard control samples or more (e.g., 2 . . . 5 . . . 10 . . . 25 . . . 50 . . . or 100 standard control samples).

In certain embodiments, at least two, three, four, or more experimental samples are assayed together. In other embodiments, multiple experimental samples are employed and these samples are successfully quantitated even though they differ in copy number from each other by 4, 5, or 6 logs (e.g., the dynamic range of the methods allows experimental samples with greatly different copy numbers to be assayed together).

In some embodiments, the threshold signal line intersects the experimental curve and two or more of the at least two standard control curves at a linear portion of these curves. In particular embodiments, the initial signal data comprises normalized signal data (e.g., normalized automatically by an assay signal reading device configured to normalize the signal or by dividing the assay signals by the signal from an internal signal control sample). In additional embodiments, the initial signal data further comprises assay signal level detected at a plurality of time intervals from an internal signal control sample. In further embodiments, the initial signal data is normalized based on the internal signal control sample or other internal signal control sample.

In particular embodiments, the slope equation is generated using linear regression. In other embodiments, the slope is a best-fit slope.

In some embodiments, the initial signal data further comprises assay signal level detected at the plurality of time intervals from at least one additional experimental sample. In other embodiments, the processing in any, all, or some of the steps is performed by a computer, or in part by a computer (e.g., by the processor of a computer). In particular embodiments, the processing in any, all, or some of the steps is performed, at least in part, manually.

In some embodiments, the present invention provides systems for displaying output results simultaneously on a single screen comprising; a) a computer system having stored therein a target quantifying software application, wherein the computer system comprises computer memory and a computer processor, and wherein the target quantifying software is configured to generate output results; and b) a user interface comprising a screen configured to display the output results from the target quantifying software application, wherein the output results are displayed simultaneously on the screen, and wherein the output results comprise: i) a first graph plotting signal over time, wherein the first graph comprises: A) at least two curves based on normalized standard control samples, and B) a threshold signal line that intersects the at least two curves (and at least one curve based on an experimental sample); and ii) a second graph plotting signal over time, wherein the second graph comprises a resulting slope fit to data points determined by the location where the threshold signal line on the first graph intersects the at least two curves.

In particular embodiments, the output results further comprise: iii) a plate display, wherein the plate display provides a visual representation of a plurality of sample wells, wherein at least a portion of the plurality of sample wells comprise the normalized standard control samples. In certain embodiments, the output results further comprise: a statistics summary box, wherein the statistics summary box comprises at least one of the following: A) an initial signal value for the threshold signal line; B) a threshold slope for the threshold signal line; or C) numerical values from the normalized standard control samples.

DESCRIPTION OF THE FIGURES

Figure 2A:
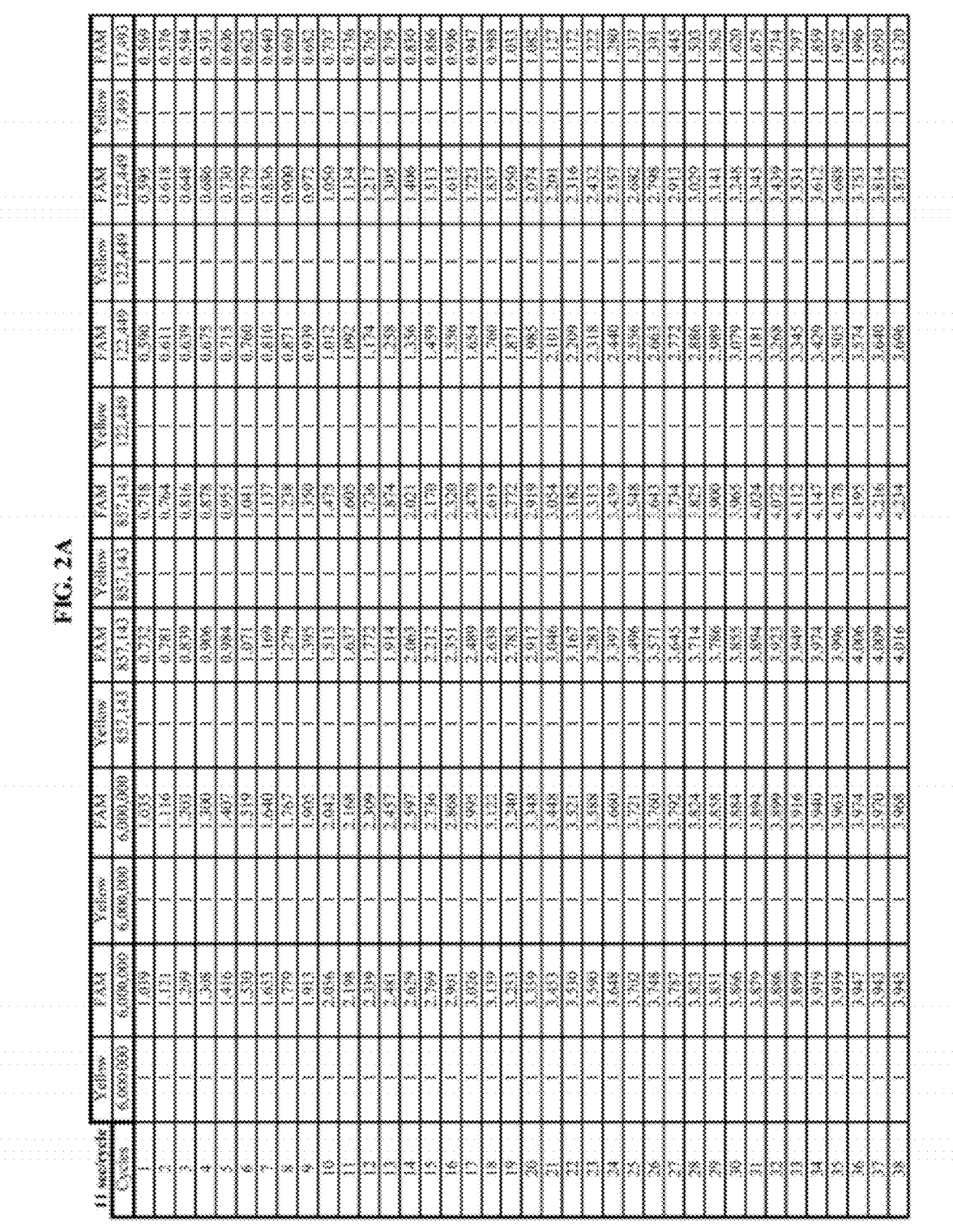
Figure 2B:
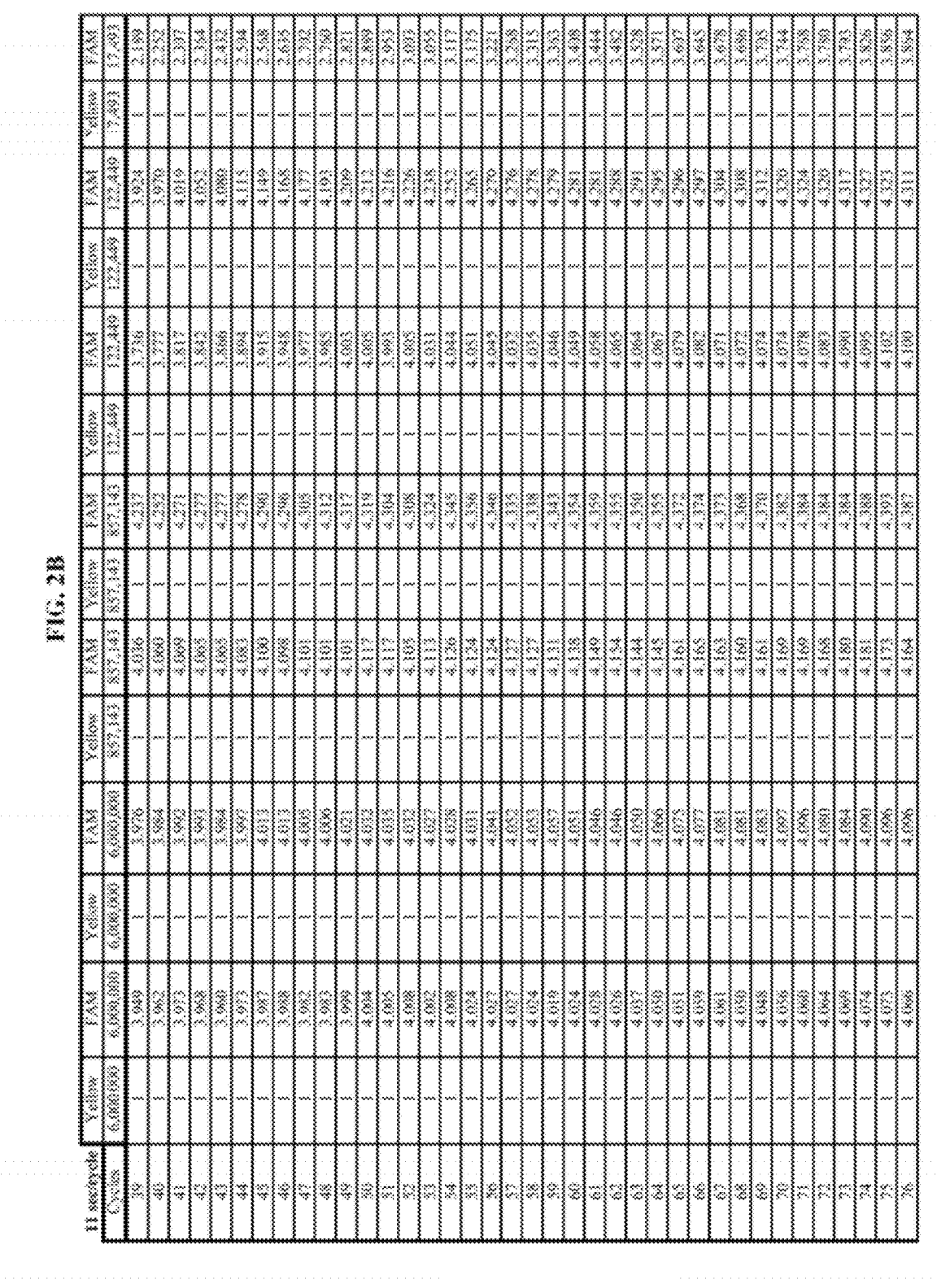
Figure 2C:
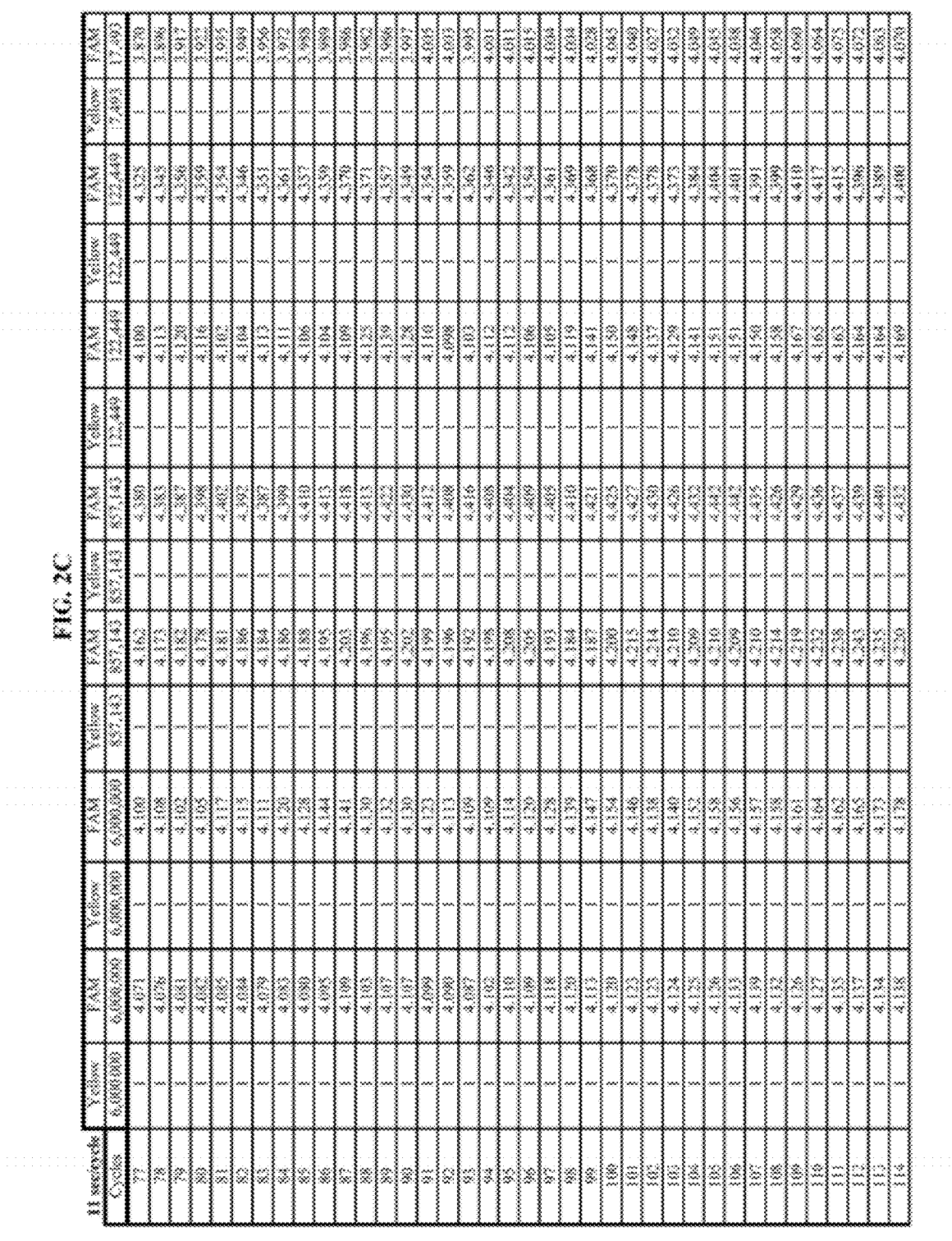
Figure 2D:
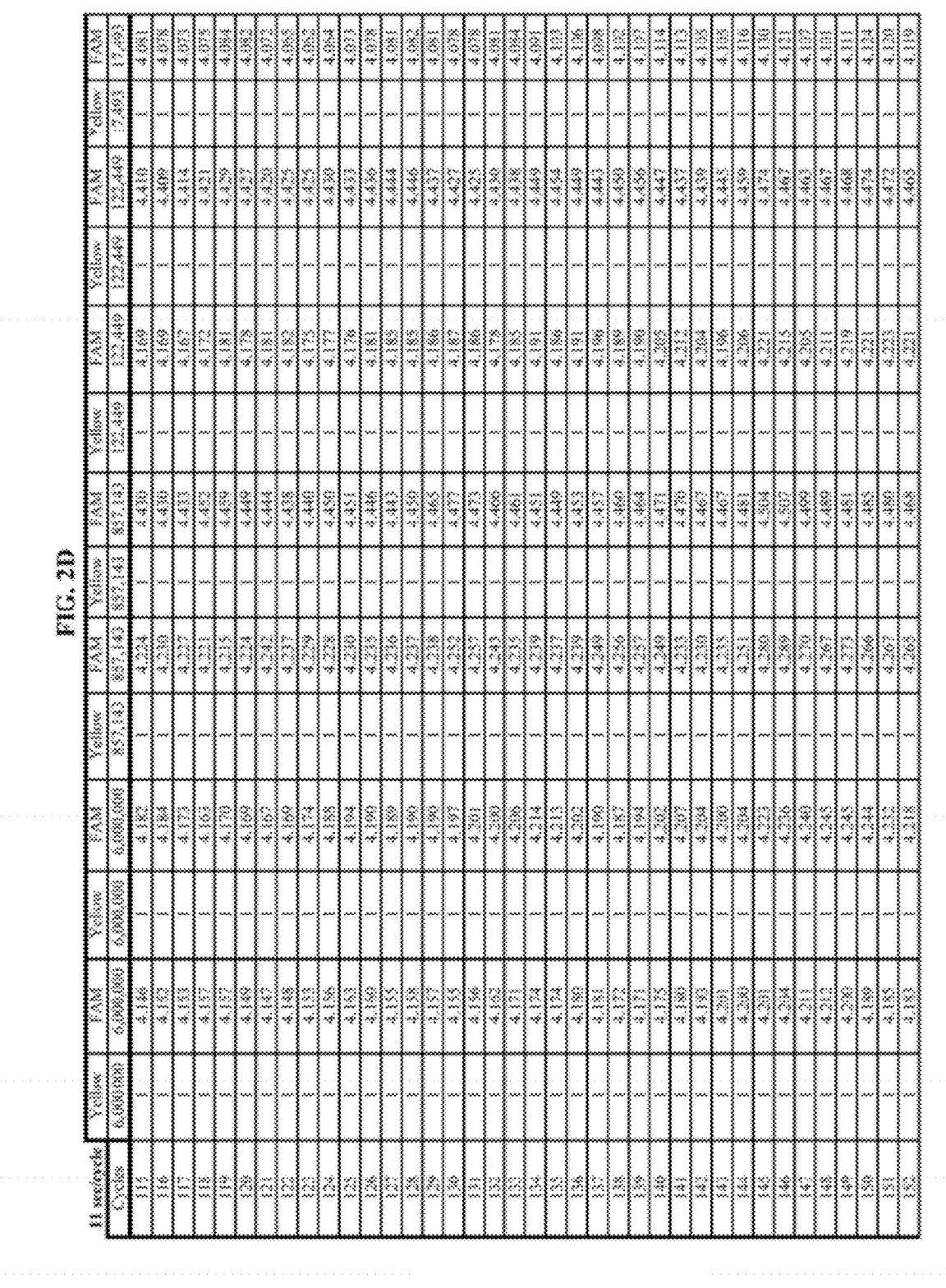
Figure 2E:
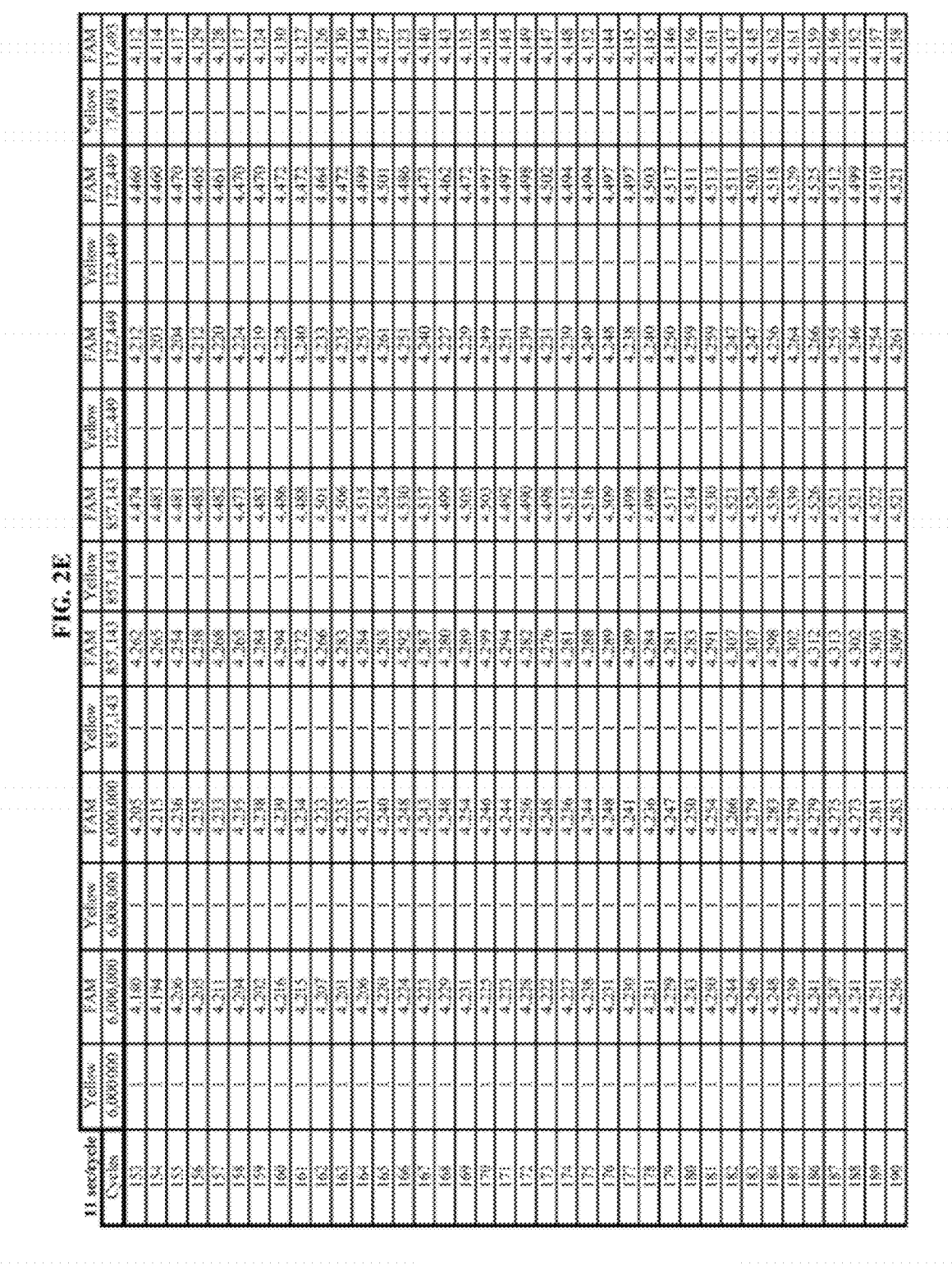
Figure 2F:
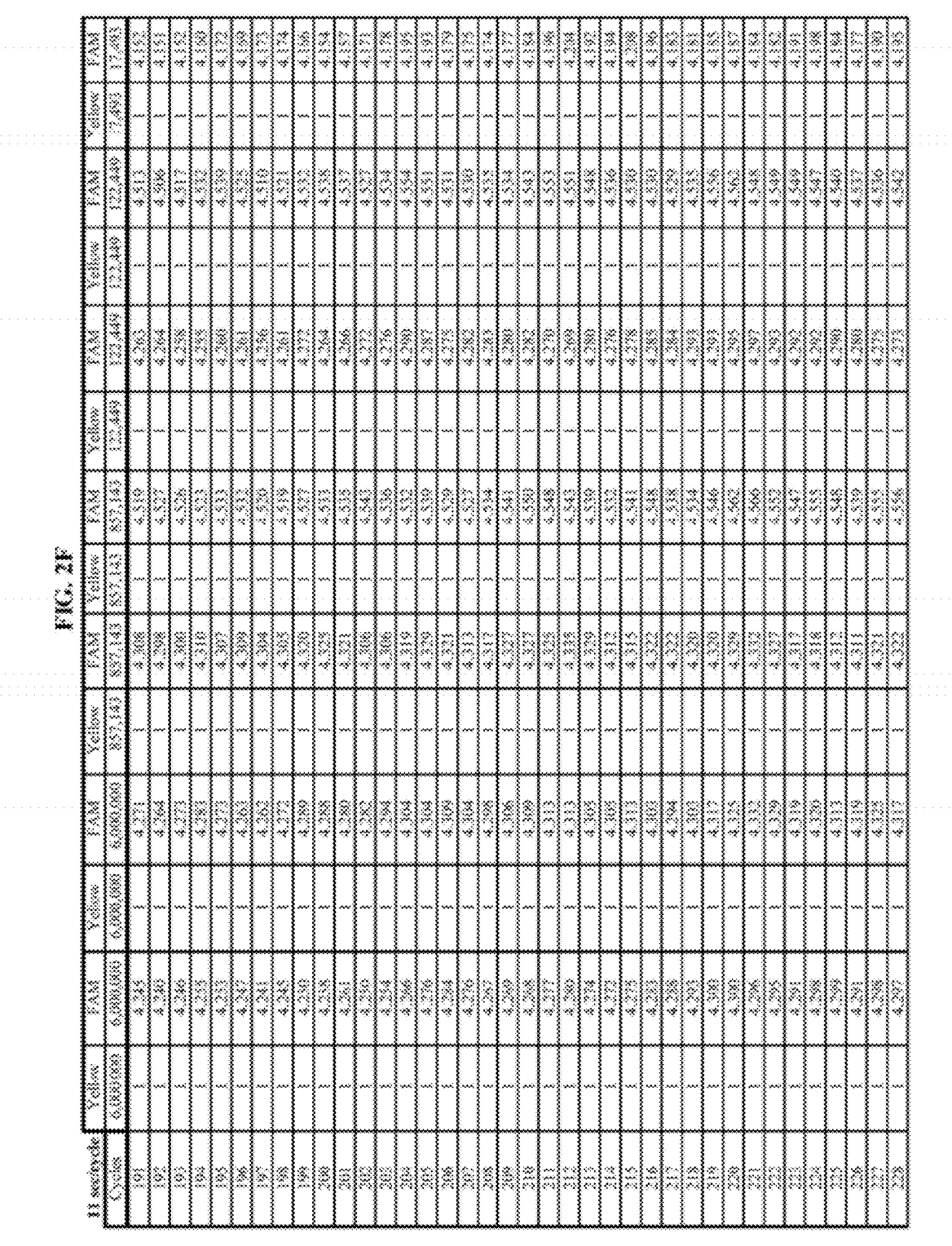
Figure 2G:
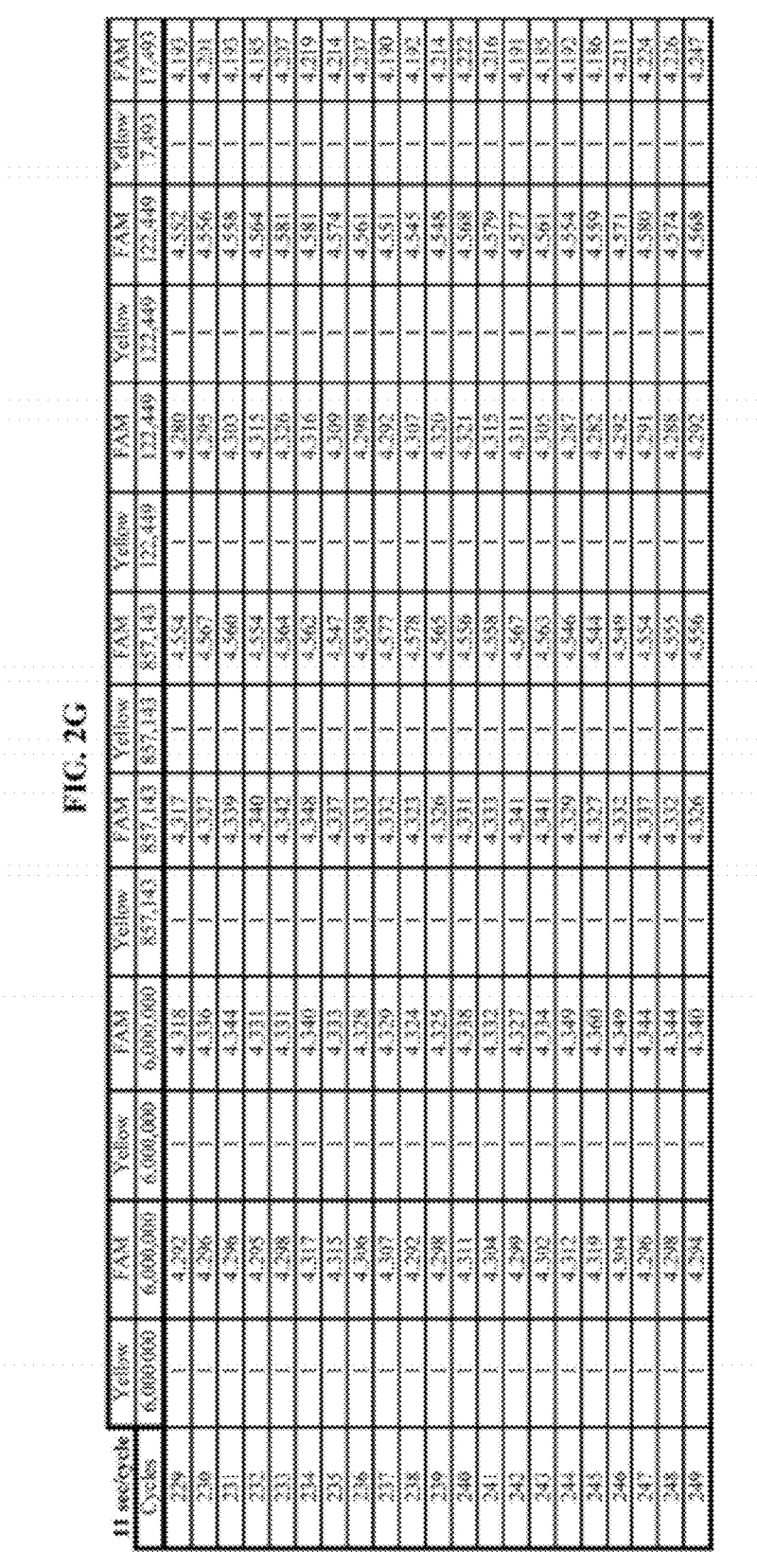
Figure 2H:
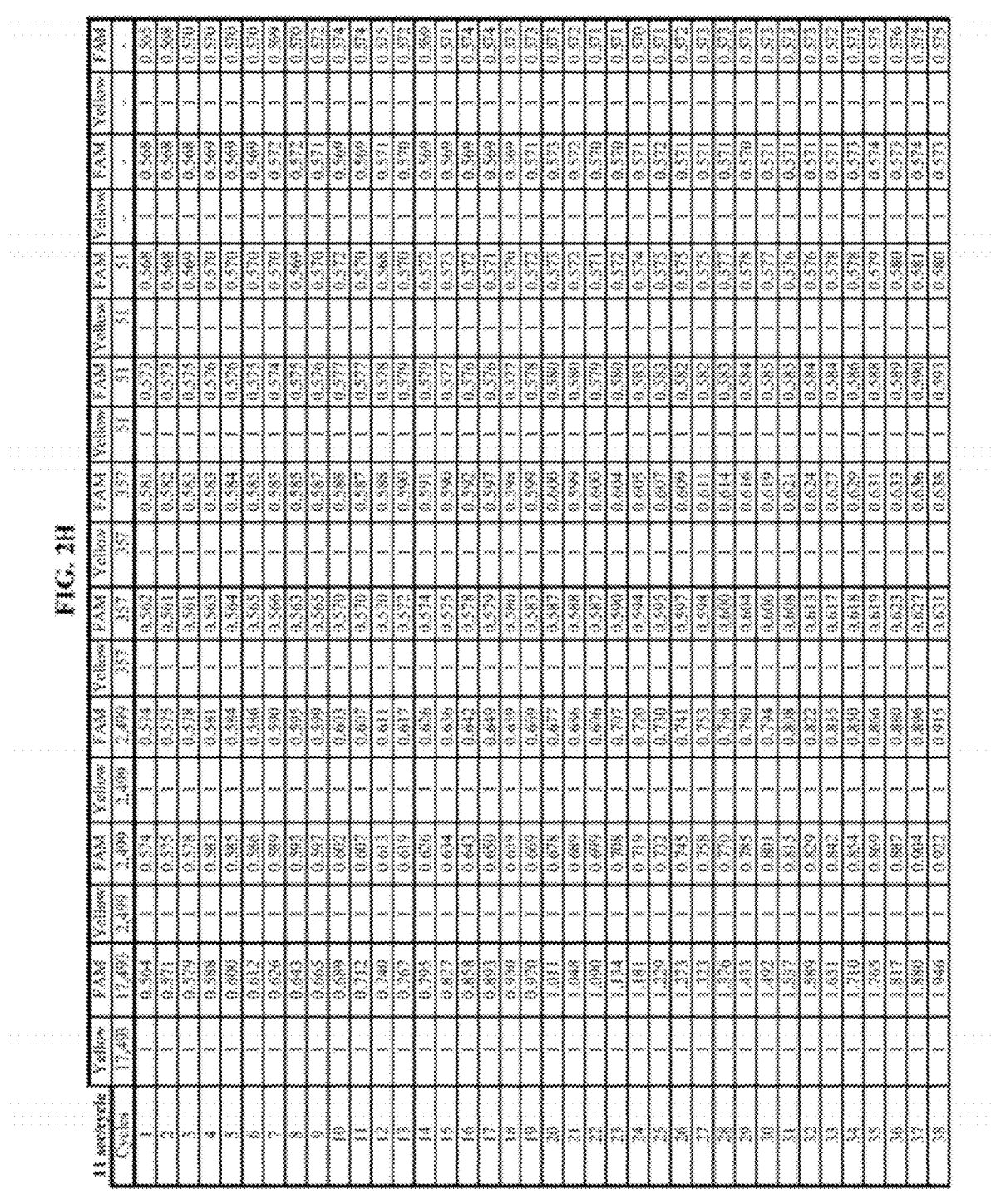
Figure 2J:
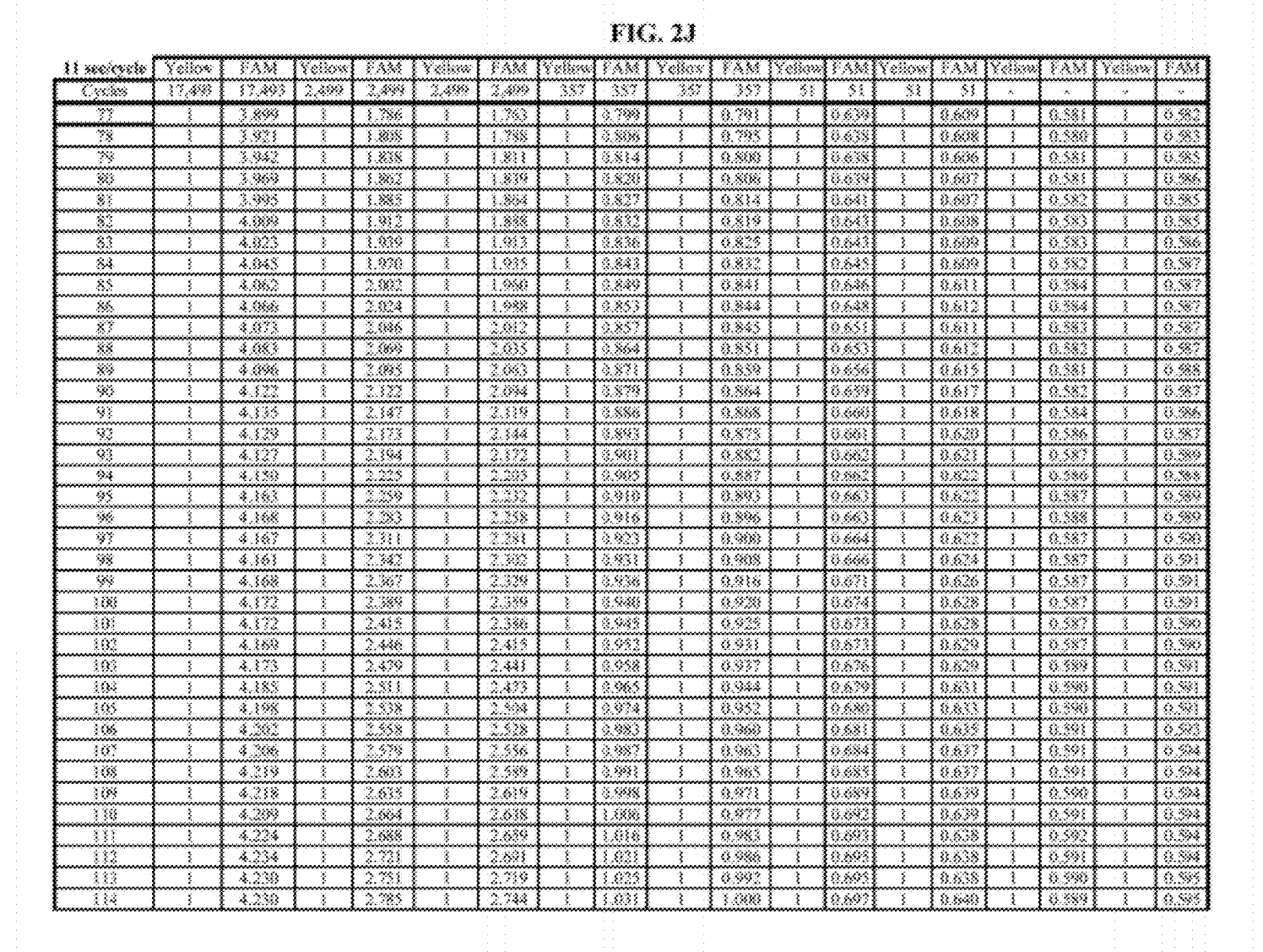
Figure 2K:
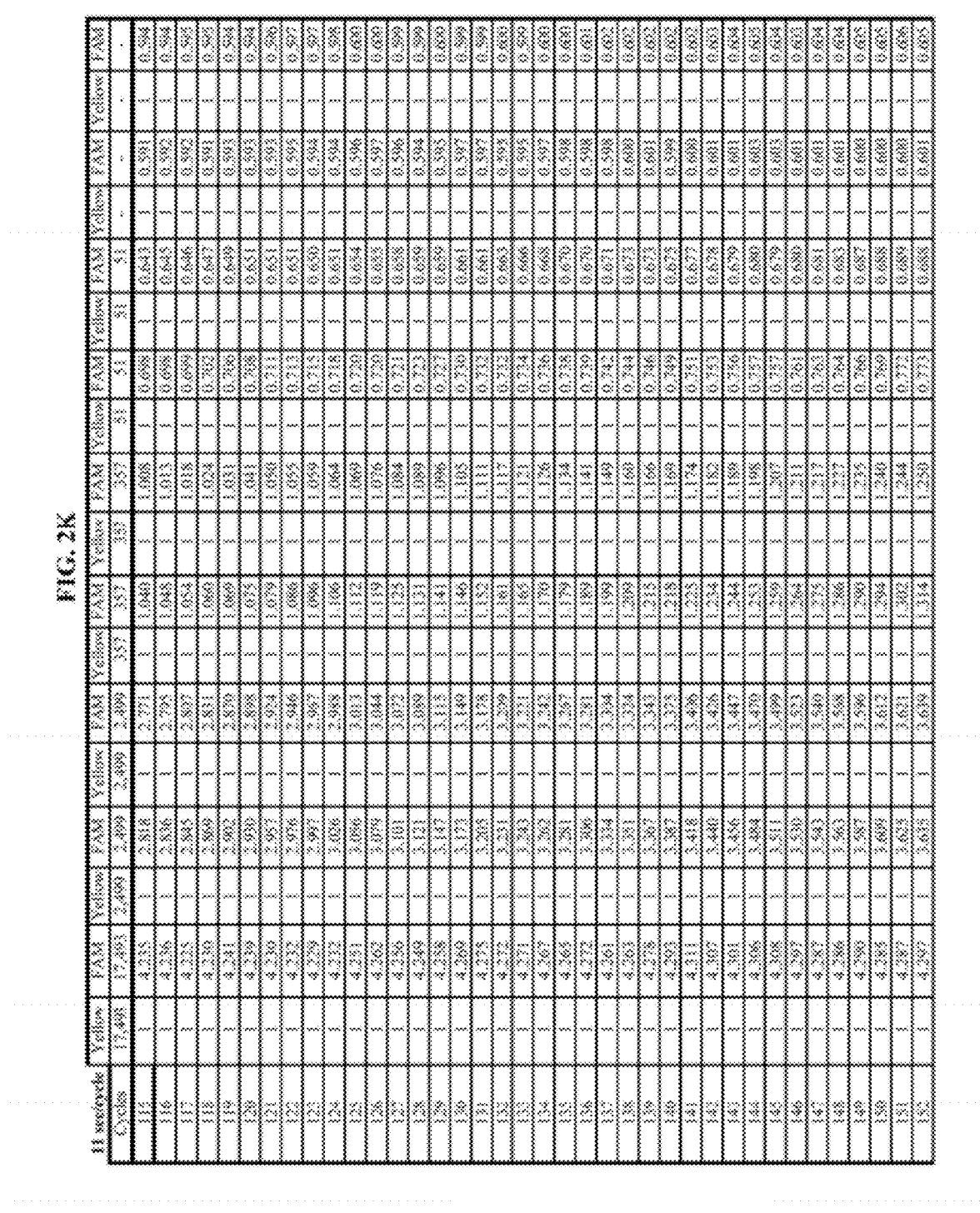
Figure 2L:
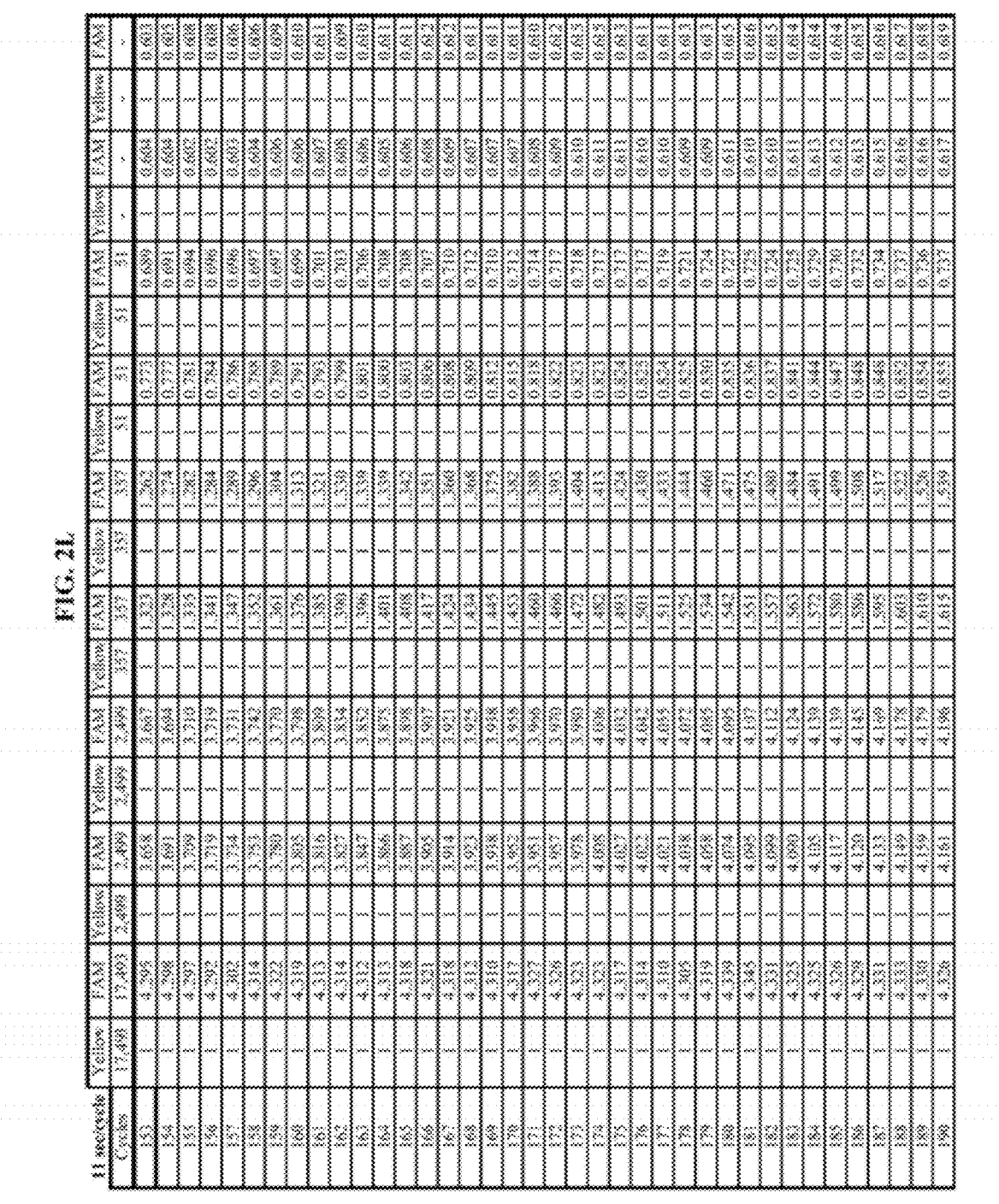
Figure 2M:
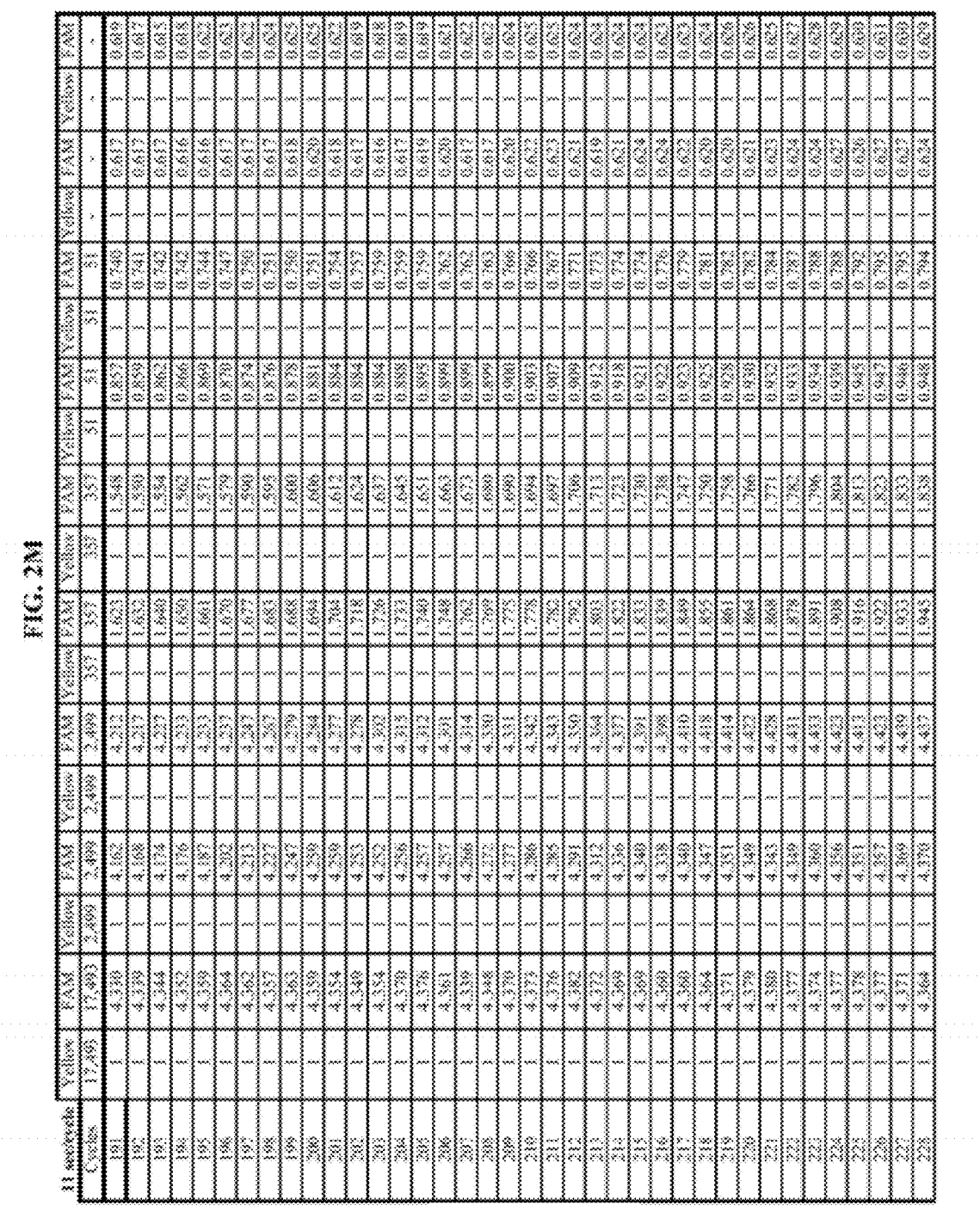
Figure 2N:
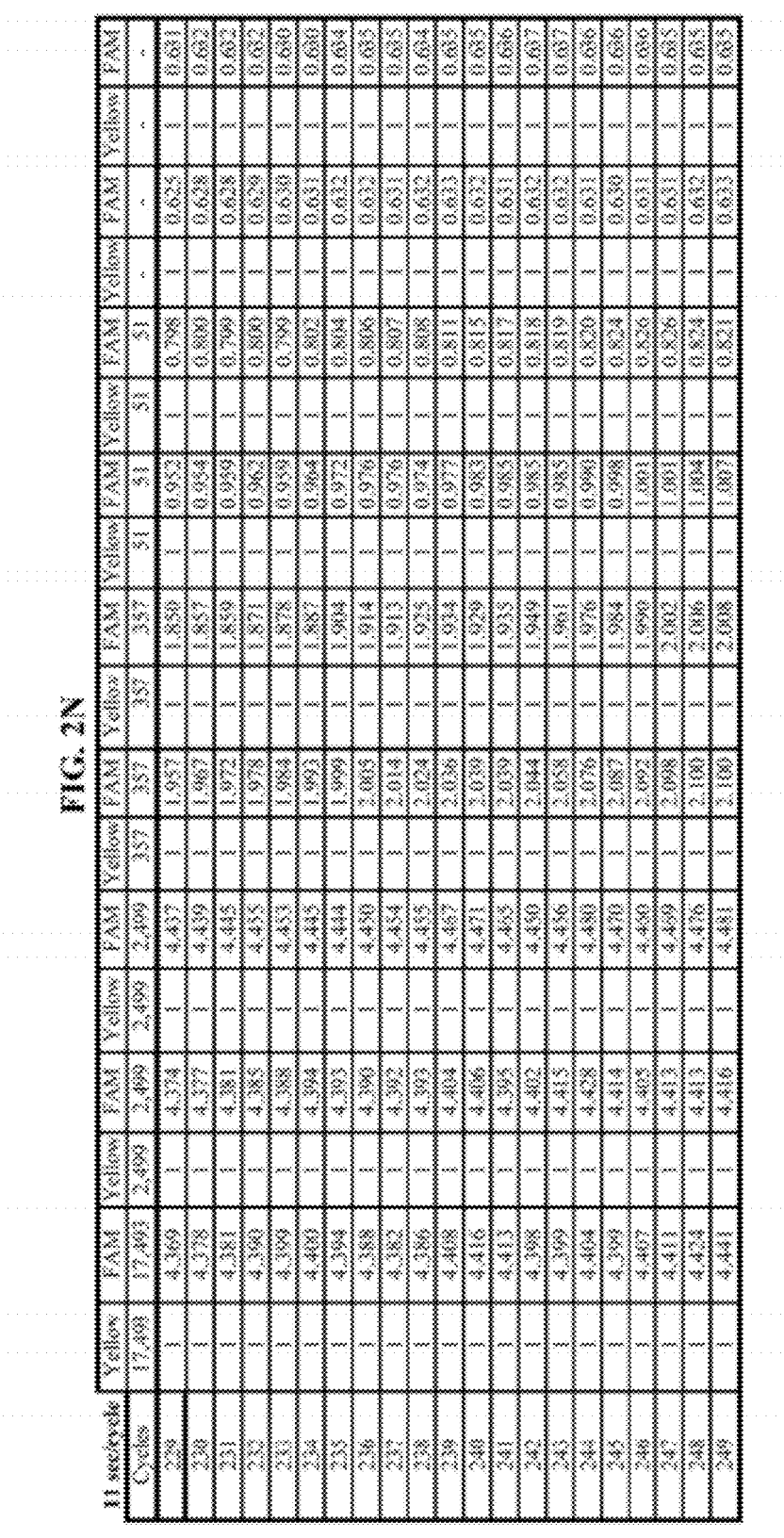

FIGS. 2A, 2B, 2C, 2D, 2E, 2F, 2G, 2H, 2I, 2J, 2K, 2L, 2M and 2N show normalized signal data from 249 time intervals (11 second intervals) from a plurality of standard control samples, run in duplicate, with different target copy numbers. FIGS. 2A and 2H show data for time intervals 1-38, FIGS. 2B and 2I show data for time intervals 39-76, FIGS. 2C and 2J show data for time intervals 77-114, FIGS. 2D and 2K show data for time intervals 115-152, FIGS. 2E and 2L show data for time intervals 153-190, FIGS. 2F and 2M show data for time intervals 191-228, and FIGS. 2G and 2N show data for time intervals 229-249.

FIGS. 3A, 3B, 3C, 3D and 3E show normalized signal data from 249 time intervals (11 second intervals) from three experimental samples (B4, E4, and F4). FIG. 3A shows data for time intervals 1-51, FIG. 3B shows data for time intervals 52-106, FIG. 3C shows data for time intervals 107-161, FIG. 3D shows data for time intervals 162-216, and FIG. 3E shows data for time intervals 217-249.

FIG. 4 shows curves generated from normalized signal data. FIG. 4 at A shows the curves generated from the normalized standard control signal data, and FIG. 4 at B shows the curves generated from the normalized experimental signal data.

FIG. 5 at A shows curves generated from normalized standard control signal data with an added threshold signal line (drawn as a horizontal line), and FIG. 5 at B shows curves generated from experimental signal data with an added threshold signal line (drawn as a horizontal line).

DESCRIPTION OF THE INVENTION

The present invention provides methods and software applications for quantifying a target in an experimental sample by collecting and processing initial signal data from the experimental sample and at least two standard control samples containing known target copy numbers. In particular embodiments, the initial signal data is capable of being plotted as an experimental curve and at least two standard control curves. In certain embodiments, the initial signal data is processed with a threshold signal line to generate control and experimental intersecting time values that can be further processed to generate log plot data comprising coordinates for a log/log plot, or linear/log plot (or similar plot). In some embodiments, the log plot data may be processed to generate a slope equation that can be used with the experimental time value to quantify target copy number in the experimental sample.

I. Exemplary Target Sequence Quantification Methods and Applications

Figure 1:
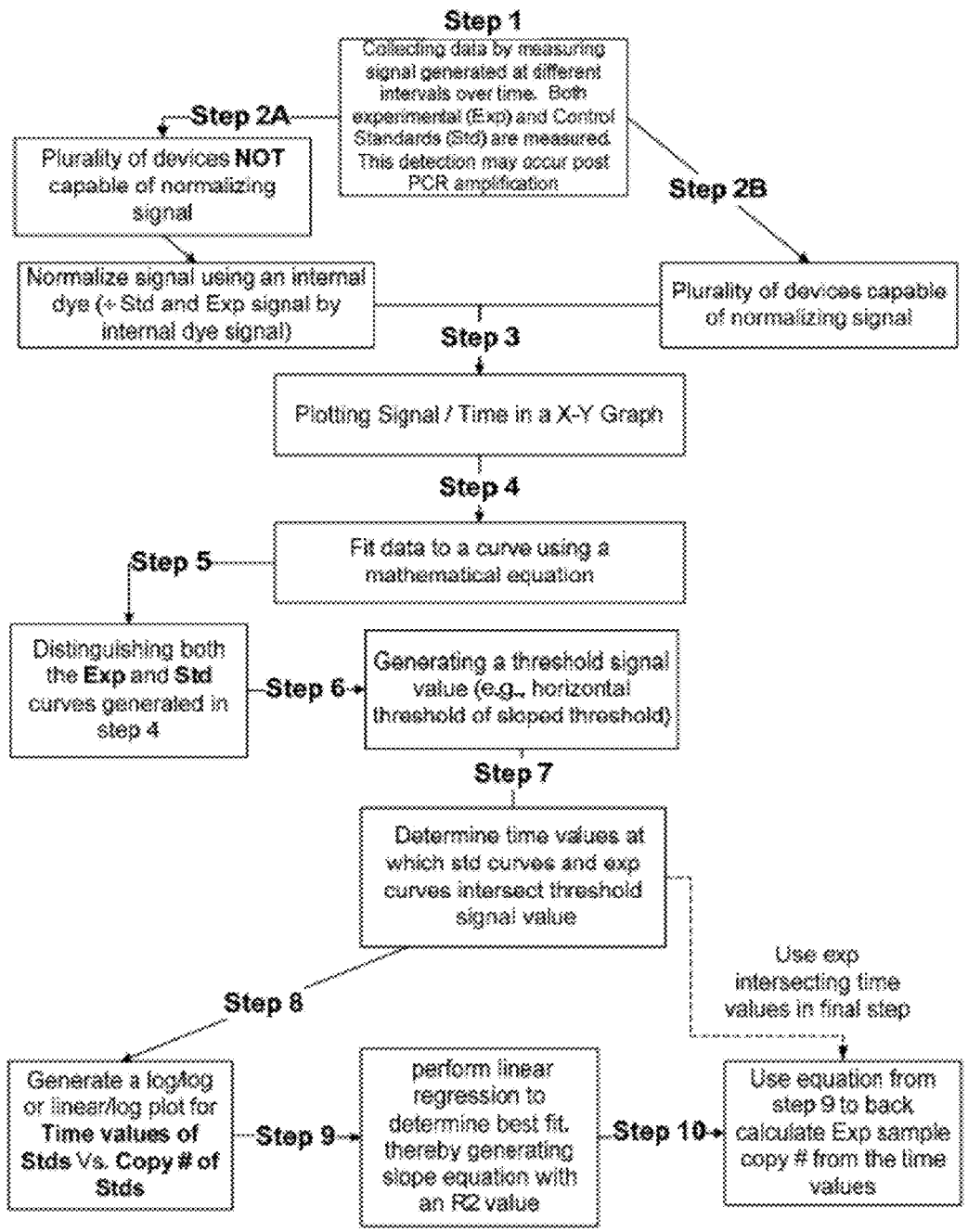
FIG. 1 shows a flow chart of one exemplary embodiment for implementing the methods and software applications of the present invention.

FIG. 1 shows an exemplary embodiment of how target sequences can be quantified in experimental samples using nucleic acid detection assays and methods that employ a threshold signal line and a log/log plot generated from standard control curves. In this exemplary embodiment, the nucleic acid detection assay is one that can generate time-course data that can be fit, using a localized linear model or other model, to fit to a curve (e.g., INVADER detection assay or other cleavage based assay). The ten exemplary steps in FIG. 1 are described below.

FIG. 1: Step 1

In Step 1 of FIG. 1, a nucleic acid detection assay is employed to detect a target sequence in both experimental and control samples. The nucleic acid detection assay generates a signal when the target is detected which can be measured over time. The nucleic acid detection assay (e.g., INVADER detection assay) employed is also one that can generate data over time that can be fit to a curve (e.g., sigmoidal or sigmoidal-like curve). In certain embodiments, the nucleic acid detection assay is run under isothermal conditions. The experimental and standard control samples may be PCR amplified prior to or during detection. A device is employed to detect the signal that is generated (e.g., a device configured to read and record a fluorescent signal in multiple samples). The device is set to detect and record the signal at various time points in each sample (e.g., every 5 seconds, every 10 seconds, every 30 seconds, or every minute).

At least two standard control samples are employed, each containing different, known amounts of the target sequence. In certain embodiments, between two and ten control samples are employed. Preferably, a standard control sample with no target is also included. In some embodiments, the target copy number in the standard control samples ranges from hundreds to millions, and values therebetween. Preferably, the control samples differ from each other by about a factor of ten.

In some embodiments, each of the standard control samples has a corresponding internal dye control sample which contains the same (or about the same) target copy number as the control sample, but is missing a component necessary for operation of the nucleic acid detection assay. In certain embodiments where a standard control sample with no target is employed, a corresponding internal dye control sample is also employed with no target. Preferably, the internal dye control sample employs a different dye than used in the standard control samples. Generally, the internal dye control samples serve to measure background signal generated by the nucleic acid detection assay. If the INVADER assay is employed, for example, the internal dye control samples may lack the INVADER oligonucleotide, but still contain the probe oligonucleotide, a Cleavase enzyme, and a FRET cassette linked to a dye different from the dye in the standard control samples. In certain embodiments, duplicates of each of the standard control samples and each of the internal dye control samples are employed. In certain embodiments, a second internal housekeeping type sequence is detected to allow, for example, relative quantification.

The target sequence that is detected can be any target sequence desired, including, for example, micro RNAs, siRNA sequences, DNA sequences, viral sequences, or other pathogen related sequences. In certain embodiments, the target sequence is a cancer related gene, or a viral sequence such as HCV, HPV, or HIV. The dyes, or other labels employed, can be any suitable dye or label including, for example, FAM, Yakima yellow internal normalizing dye, Cy3, Cy5, and other dyes known in the art.

FIG. 1: Steps 2A and 2B

In general, if the results are obtained on a device that is not capable of normalizing the signal, then, as shown in Step 2A of FIG. 1, normalized signals can be obtained by dividing the signal from the standard control samples and experimental samples with the corresponding signal from the internal dye control samples. If the results are obtained on a device capable of normalizing the signal automatically, as shown in Step 2B, then no additional processing is necessary to obtain normalized results. One example of normalized results for standard control samples is shown in FIGS. 2A, 2B, 2C, 2D, 2E, 2F, 2G, 2H, 2I, 2J, 2K, 2L, 2M and 2N, and one example of normalized results for experimental samples is shown in FIGS. 3A, 3B, 3C, 3D and 3E.

FIG. 1: Step 3

In certain embodiments, the normalized standard control and experimental samples are plotted on an X-Y graph in a signal versus time manner.

FIG. 1: Step 4

The normalized standard control and experimental sample signals can then fit to a curve using any number of known mathematical equations (there are, for example, about 50 well known mathematical equations that can be used for such purpose). Preferably, this function is performed by a computer program configured to generate such curves. In certain embodiments, equations are employed that fit each two signal data points to a line to generate the curve, while in other embodiments spline interpolation is employed. One example of fitting signal data to a curve is shown in FIG. 4, with the standard control curves shown in FIG. 4 at A and the experimental curves shown in FIGS. 4 at B.

FIG. 1: Step 5

Then, in certain embodiment (while not necessary in other embodiments) a method is employed to distinguish the standard control curves from the experimental curves, such as using sample position ID or other associated data.

FIG. 1: Step 6

Next, a threshold signal line is determined (e.g., either automatically by a software application or by a user). For convenience, as shown in FIG. 5 at A and in FIG. 5 at B, this threshold signal line can be drawn as a horizontal line on the standard control and experimental curve graphs. It is noted that other, non-horizontal lines (e.g., sloping thresholds and/or curved lines) maybe employed. It should be understood that the threshold signal line may not actually be shown (e.g., on a computer screen) as a line, but instead may be represented in computer memory as an equation that would describe a line if it were drawn and presented to a user (e.g., on a computer screen). In certain embodiments, the threshold signal line is a curve (i.e., not a straight line).

A threshold signal line will have an initial signal value at time zero. Even if the line is now drawn back to zero (e.g., the first read is not until 15 seconds or so), the threshold signal line could be extended back until hitting the Y axis to determine what signal value would be present for the line at time zero. A threshold signal line will also have a slope, which may be zero (horizontal line), negative (downward sloping line) or positive (upward sloping line). The signal line may be linear or may be a curve. A displayed threshold line may be moved by the use to any desired position or slope.

The threshold signal line can, for example, be set at any level that: 1) is above background levels (e.g., above the normalized internal dye control value); 2) intersects the experimental curve; and 3) intersects at least two of the standard control curves. In certain embodiments, additional criteria may be employed. For example, the threshold signal line may be chosen such that is intersects more than two standard control curves if there are more than two present. In certain embodiments, the threshold signal line is chosen such that it intersects all or most of the standard control curves. In other embodiments, if multiple experimental curves are present, the threshold signal line is chosen such that it intersect at least two of these curves, and preferably all of these curves.

In particular embodiments, the threshold signal line is chosen such that any variability between duplicate standard control curves (if duplicate samples are assayed) are minimized. In other embodiments, the threshold signal line is chosen such that the linear portion of most or all of the curves (e.g., the curves of interest) are intersected. In certain embodiments, multiple threshold signal lines are chosen and employed in the remainder of the steps. In some embodiments, multiple threshold signal lines are chosen (e.g., by use or by computer software) such that the $R^2$ values that result may be compared. In particular embodiments, the threshold signal line that gives the higher $R^2$ value (e.g., closest to 1.0) is chosen as the value used to calculate the copy numbers in the unknown samples. The $R^2$ may be measured using all of the points in the in the curve or a sub-set thereof. For example, data points that either extreme may be deselected so as to not be included in the best fit calculation. This finds use, for example, where the most accurate prediction is desired for a sub-set of the samples within a particular concentration range.

In certain embodiments, a sloping threshold signal line is employed. In particular embodiments, a sloping threshold signal line is employed such that many or all of the curves (e.g., both control and experimental curves) are intersected. In some embodiments, as explained below, the resulting intersection points are plotted on a log/linear chart (copy number vs. time) rather a log/log chart.

FIG. 1: Step 7

The threshold signal line (or values) is then used to determine the time value where each of the relevant standard control and experimental curves intersects the threshold. This can be done for example, by using a graph of the standard control curves (e.g., FIG. 5 at A) and experimental curves (e.g., FIG. 5 at B) and looking to see at what point in time where the threshold intersects each curve. This can also be done using a software application that automatically calculates the intersection points. The results of this determination can, for example, be charted in a table listing target copy number for each of the standard control curves and time value where the standard control and experimental curves intersect the threshold.

FIG. 1: Step 8

Figure 6:
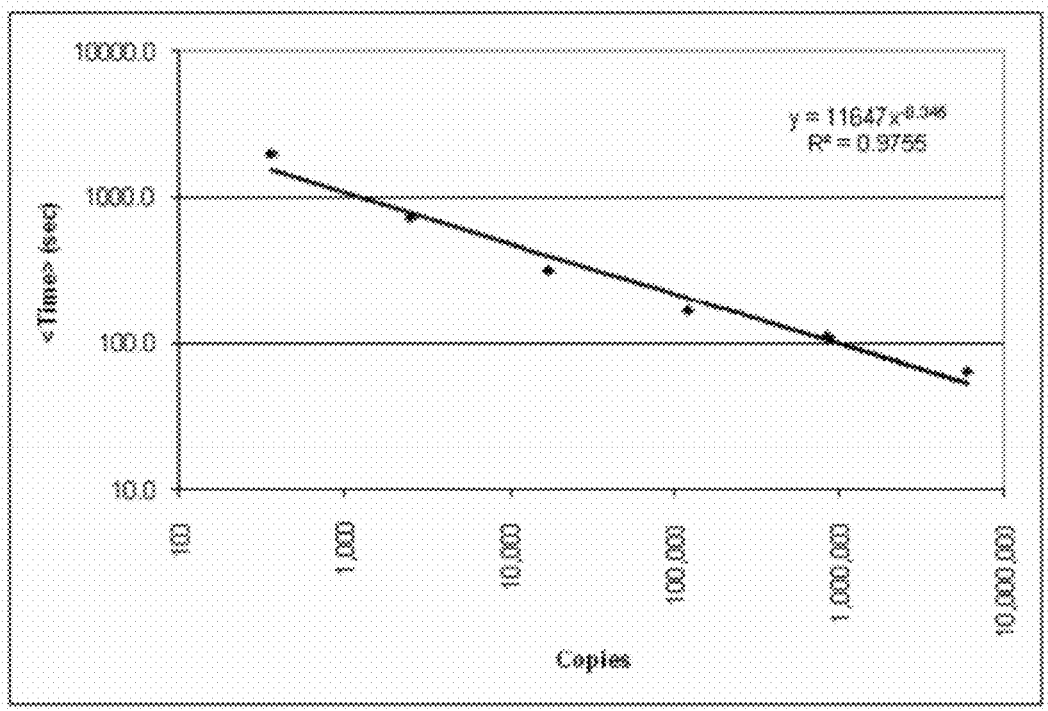
FIG. 6 shows standard control intersecting time values in a log/log plot of time values versus target copy numbers and a slope (and slope equation) fit to the values on the log/log plot.

The intersecting time values for each standard control curve can then be plotted against the target copy number of each standard control in a log/log plot, or a log/linear plot (copy number vs. time), to generate log plot data which can be aligned in a generally linear slope. Preferably, the plot is generated with copy number along the X-axis and the time along the Y-axis. An example of six standard controls plotted on a graph is shown in FIG. 6.

FIG. 1: Step 9

Next, standard linear regression methods are employed to determine the best fit for a slope between the plotted data points from Step 8. Determining this slope generates a slope equation describing the slope, as well as an $R^2$ value for the resulting slope. In certain embodiments, the threshold signal line (which may be described by a slope equation) is tested at many different positions (e.g., automatically by a computer) such that multiple $R^2$ values are determined. In certain embodiments, the threshold signal line that has an $R^2$ value that is the highest (e.g., closest or equal to 1.0) is chosen for use in determining the copy numbers in the experimental samples (e.g., used in Step 10 below).

FIG. 1: Step 10

Plugging in the intersecting time values determined for the experimental samples (from Step 7) into the slope equation determined in Step 9 allows a back calculation of the target copy number in the experimental sample(s). In certain embodiments (e.g., computer software aided embodiments) where samples are being read in real time, once an target copy number is determined for a given experimental sample (or all experimental samples) the data collection can be stopped (e.g., no need to continue the sample reading of signal once answer is achieved). This is useful as extra time and resources can be saved by stopping a real time read (e.g., another set of samples could be loaded into the reading device). This is particularly useful where the software is configured to use multiple threshold signal lines, including angled thresholds, where an answer is achieved quickly (e.g., 10-20 minutes), such as when a certain $R^2$ value is achieved for a given threshold.

In certain embodiments where multiple threshold signal lines are employed, the software may be configured to report an experimental copy number result once a particular $R^2$ value is achieved based on any of the thresholds. In other embodiments, the use of multiple threshold signal values (e.g., all employed or all that meet a minimum $R^2$ value for the resulting slope) allows a range of results to be reported for the experimental (unknown) samples. For example, when multiple threshold signal values are employed, it may be that five generate resulting slopes that have $R^2$ values above 0.98. These five results may lead to an experimental copy number in a sample of 29, 36, 38, 42, and 45. In turn, this allows the software to report a range for the experimental sample (e.g., 29-45 copies in the unknown sample). Likewise, generation of a range may be used in conjunction with limits that are set (e.g., FDA mandated limits), such as, for example, in blood screening. Any particular blood sample that has too many target copies numbers of a particular target may be deemed as "failed" (e.g., if the cut off range is 30, and a range of 29-45 is reported, this sample is deemed to have failed even though setting the threshold at other higher $R^2$ value levels would have caused the sample to "pass."). Thus, in some embodiments, the lowest predicted copy number result is used to select a course of action. In other embodiments, where a minimum amount of a target is required, the system requires that each of the curves report a result above a predetermined copy number in selecting a course of action.

II. Rapid Quantitative Results

The methods and applications of the present invention allow surprisingly rapid quantitation of copy number in an experimental sample. Methods known in the art often require an hour or hours to provide reliable quantitative results. However, the present invention allows reliable quantitative results to be achieved in time values measured in second or minutes. For example, in particular embodiments, the quantified target copy number in the experimental sample is generated within about 150 seconds or less from the time when an assay signal level is first detected from the experimental sample (e.g., within about 75 seconds . . . about 100 seconds . . . about 125 seconds . . . or about 150 seconds). In some embodiments, the quantified target copy number in the experimental sample is generated within about 45 minutes or less from the time when an assay signal level is first detected from the experimental sample (e.g., within about 5 minutes . . . about 15 minutes . . . about 30 minutes . . . or about 45 minutes). In certain embodiments, the quantified target copy number in the experimental sample is generated between about 2 minutes and about 35 minutes from the time when an assay signal is first detected from the experimental sample.

Rapid quantification may be achieved with the methods of the present invention as reliable quantitative information can be produced once at least two standard control signmoidal curves and the experimental curve pass the threshold signal line, which often happens very early for many experimental samples. For example, FIG. 5 at A and in FIG. 5 at B shows the standard control and experimental curves from Example 1. Experimental sample B4 (shown in FIG. 5 at B) is seen to pass the threshold at about 110 seconds. Three of the standard control curves, as shown in FIG. 5 at A, all pass the threshold by about 120-130 seconds. Consequently, the target copy number in experimental sample B4 could be calculated after about 130 seconds from the initial signal detection in the experimental sample. This rapid quantitation could be even further reduced for the B4 sample if the threshold signal line were set lower than the 1.6 shown in FIG. 5. For example, the threshold could be set anywhere above 1.0 (which represents the background signal) and still intersect each of the three standard control curves and the B4 experimental curve. For example, the threshold signal line could be set at about 1.1, which would allow quantitative results to be achieved at about 105-110 seconds.

In certain embodiments, the threshold signal line is set as a non-horizontal slope (e.g., downward slope) which may allow more curves to be intersected sooner. In such embodiments, quick quantitative results can be obtained, as one does not have to wait for the curves of interest to reach a horizontal threshold signal line. In such embodiments, results may be achieved in 20 minutes or less or 15 minutes or less (e.g., between 12 and 15 minutes; or between 5-10 minutes; or between 1-5 minutes).

Preferably, the methods of the present invention are embodied in a software application on a computer that is operably linked to the signal detection device. In this regard, curves could be generated automatically (and quickly), and once the requisite curves have passed the threshold signal line, the final quantitative copy number in the experimental sample can be calculated rapidly (e.g., in a second or less), thereby allowing a user to have a quantitative copy number as rapidly as possible.

III. Exemplary Nucleic Acid Detection Assays

The methods and systems of the present invention may be employed with any nucleic acid detection assay that can generate results over time that can be fit to a curve. For example, the methods, systems, and applications of the present invention may find use in detection assays that include, but are not limited to, enzyme mismatch cleavage methods (e.g., Variagenics, U.S. Pat. Nos. 6,110,684, 5,958, 692, 5,851,770, herein incorporated by reference in their entireties); polymerase chain reaction; branched hybridization methods (e.g., Chiron, U.S. Pat. Nos. 5,849,481, 5,710, 264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Barnay Proc. Natl. Acad. Sci USA 88, 189-93 (1991)); FULL-VELOCITY assays; and sandwich hybridization methods (e.g., U.S. Pat. No. 5,288,609, herein incorporated by reference in its entirety).

Preferably, the nucleic acid detection assay is configured to run under isothermal conditions. One example of such a nucleic acid detection assay is an invasive cleavage assay, such as the INVADER assay. In INVADER assay, when two strands of nucleic acid, or oligonucleotides (the probe oligonucleotide and the INVADER oligonucleotide), both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide (INVADER oligonucleotide), the cleavage agent can be made to cleave the downstream oligonucleotide (probe) at an internal site in such a way that a distinctive fragment is produced. Such embodiments have been termed the INVADER assay (Third Wave Technologies) and are described in U.S. Pat. Nos. 5,846,717, 5,985,557, 5,994,069, 6,001,567, and 6,090,543, WO 97/27214 WO 98/42873, Lyamichev et al., Nat. Biotech., 17:292 (1999), Hall et al., PNAS, USA, 97:8272 (2000), each of which is herein incorporated by reference in their entirety for all purposes). The INVADER assay detects hybridization of probes to a target by enzymatic cleavage of specific structures by structure specific enzymes.

The INVADER assay detects specific DNA and RNA sequences by using structure-specific enzymes (e.g. FEN endonucleases) to cleave a complex formed by the hybridization of overlapping oligonucleotide probes. Elevated temperature and an excess of one of the probes enable multiple probes to be cleaved for each target sequence present without temperature cycling. In some embodiments, these cleaved probes then direct cleavage of a second labeled probe (e.g., FRET cassette). The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay can detect specific mutations and SNPs in unamplified, as well as amplified, RNA and DNA including genomic DNA. In certain embodiments, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations. In the primary reaction, the WT primary probe and the INVADER oligonucleotide hybridize in tandem to the target nucleic acid to form an overlapping structure. An unpaired "flap" is included on the 5' end of the WT primary probe. A structure-specific enzyme (e.g. the CLEAVASE enzyme, Third Wave Technologies) recognizes the overlap and cleaves off the unpaired flap, releasing it as a target-specific product. In the secondary reaction, this cleaved product serves as an INVADER oligonucleotide on the WT fluorescence resonance energy transfer (WT-FRET) probe to again create the structure recognized by the structure specific enzyme. When the two dyes on a single FRET probe are separated by cleavage, a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In preferred embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the target nucleotide sequence do not match perfectly at the cleavage site, the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

In the INVADER assays, the probes turn can over without temperature cycling to produce many signals per target (i.e., linear signal amplification). Similarly, each target-specific product can enable the cleavage of many FRET probes. The primary INVADER assay reaction is directed against the target DNA (or RNA) being detected. The target DNA or RNA is the limiting component in the first invasive cleavage, since the INVADER and primary probe are supplied in molar excess. In the second invasive cleavage, it is the released flap that is limiting. When these two cleavage reactions are performed sequentially, the fluorescence signal from the composite reaction accumulates linearly with respect to the target DNA amount.

IV. Genotyping Applications

Besides the use of the methods, systems, and software applications of the present invention to determine copy number in sample, the present invention is also useful for genotyping. One exemplary embodiment of such use is with the INVADER detection assay. A genotyping INVADER reaction, were two probes differing at the base of cleavage and corresponding to the base change or genotype of the target can be used by having two different 5'-flaps attached to the probes. Upon cleavage of the 5'-flap, a secondary cleavage of a FRET cassettes can be obtained by using the cleaved flap as an invasive oligo on the FRET cassette. The FRET cassettes are labeled with different dyes (e.g., FAM and RED) corresponding to the genotype-specific cleaved primary probe.

A typical genotyping real-time INVADER assay may be performed by monitoring FAM and RED fluorescence signal as a function of time. A threshold for each dye that is above the background level is assigned and time points at which each sample crosses the threshold for each dye are determined. Plotting a scatter plot of threshold times of FAM versus RED will result in a scatter plot that can be used to determine genotypes of unknown samples. Samples with low FAM times and high RED times correspond to the FAM probe or allele and those with high FAM and low RED times correspond to the RED probe or allele. Similarly, samples with moderate FAM and RED times (i.e, fall in the middle of the scatter plot) are heterozygous samples. This same approach can also be employed with other nucleic acid detection assays.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); C (degrees Centigrade); and R2 ($R^2$).

EXAMPLE 1

Target Sequence Quantification Using a Threshold and Log/Log Plot

This example describes quantifying the copy number of a target sequence in three unknown experimental samples using a nucleic acid detection assay that can generate a detection curve and using methods that employ a threshold and log/log plot generated from standard control curves. The target sequence in this example was micro RNA miR-21, and the nucleic acid detection assay was the INVADER nucleic acid detection assay employing a FRET cassette with a FAM label.

The seven known standards employed had the following target copy numbers: 1) 6×10⁶; 2) 857, 143; 3) 122, 449; 4) 17, 493; 5) 2, 499; 6) 357; and 7) 51.

A normalizing dye-labeled oligonucleotide was added to the reaction to account for signal fluctuations due to machine noise of pipetting errors. This dye-labeled oligonucleotide does not interfere or function in the INVADER reaction and is spectrally distinct and differentiated from the dye used in INVADER reaction FRET cassette. Yakima yellow labeled oligonucleotide ($T_{10}$) was used as internal normalizing dye (25 nM) and was included in the wells of all the reactions. Three experimental samples tested were labeled B4, E4, and F4. These samples were run with the FAM labeled FRET as well as with the internal Yellow dye.

PCR was initially performed on both the standards and the experimentals using the parameters shown in Table 1.

TABLE 1

| Stage | Temperature | Time | Cycles | Data Collection |
|---|---|---|---|---|
| 1 | 42° C. | 45 min | 1 | Off |
|   | 95° C. | 2 min |   |   |
| 2 | 95° C. | 30 sec | 22 | Off |
|   | 60° C. | 1 min |   |   |
| 3 | 99° C. | 10 min | 1 | Off |
| 4 | 50° C. | 11 sec | 255 | ON |

INVADER assay reagents (e.g., probe oligos, INVADER oligos, FRET cassettes, and a Cleavase enzyme) were then added to the experimental, standard control, and internal control samples. Reactions were run at 50 degrees Celsius and fluorescent signal readings were taken every 11 seconds for 249 cycles.

The results from the standard controls and internal controls (normalized based on the internal dye control) are shown in FIGS. 2A, 2B, 2C, 2D, 2E, 2F, 2G, 2H, 2I, 2J, 2K, 2L, 2M and 2N. The results for the three experimental samples (normalized based on the internal dye control) are shown in FIGS. 3A-3E. The normalized results from FIGS. 2A, 2B, 2C, 2D, 2E, 2F, 2G, 2H, 2I, 2J, 2K, 2L, 2M, 2N, 3A, 3B, 3C, 3D and 3E were then plotted (fluorescence vs. time) in an X-Y graph. The normalized plots from FIGS. 2A, 2B, 2C, 2D, 2E, 2F, 2G, 2H, 2I, 2J, 2K, 2L, 2M, 2N, 3A, 3B, 3C, 3D and 3E were then fit to a curve using a program that fits each two data points to a line. The results of this are shown in FIG. 4. For convenience, the standard control curves are shown in FIG. 4 at A, and experimental curves are shown in FIG. 4 at B.

Next, a threshold signal line was determined, which can be drawn onto the curve graphs shown in FIG. 4. The threshold signal line is set at a fluorescent signal level based on the following exemplary criteria. First, the threshold value is set at a signal level that is greater than the background represented by the normalized internal dye controls (those samples with the Yellow internal dye). In this example, the normalized signal from the internal dye controls is 1.0 as dividing the raw numbers obtained by themselves leads to a value of 1.0. Next, the threshold signal line is set so that it intersects all of the standards control and experimental curves that are above the background (above 1.0 in this example). In this example, experimental sample F4 only extends up to 1.7. As such, to intersect this curve, and all other curves, the threshold is chosen to be below about 1.7. Another parameter that could be employed, but that does not affect the threshold in this example, is choosing a threshold that minimizes the variability between the two duplicate curves for each standard. In light of the above criteria, the threshold signal line for this example could be set anywhere between 1.0 and about 1.7. However, one additional parameter that is preferentially employed, is setting the threshold value such that the signal growth portion of most or all of the curves is intersected. In this example, in order to ensure that that the signal growth portion of all the standard and unknown curves were intersected at a non-saturating point in the curves, the final threshold value was set around 1.6. FIG. 5 shows the threshold signal line depicted as a horizontal line set at about 1.6 for both the standard control curves (FIG. 5 at A) and the experimental curves (FIG. 5 at B).

Once the threshold signal line is set, this allows a determination of the time point where each of the standard control curves intersects the threshold signal line. In this example, it was determined that the threshold signal line intersects the standard control curves at the time points shown in Table 2 below.

TABLE 2

| miR-21 copies/rxn | Time 1 (sec) | Time 2 (sec) | Average Time (sec) | Stdev |
|---|---|---|---|---|
| 6,000,000 | 63.0 | 64.1 | 63.6 | 0.4 |
| 857,143 | 108.7 | 112.0 | 110.4 | 1.2 |
| 122,449 | 169.4 | 163.6 | 166.5 | 2.1 |
| 17,493 | 307.5 | 332.0 | 319.7 | 8.7 |
| 2,499 | 722.9 | 731.5 | 727.2 | 3.0 |
| 357 | 1934.8 | 2036.1 | 1985.4 | 35.8 |

Surprisingly, it was found that the average intersecting time values for each of the six standards can be plotted against the target copy number of the standards in a log vs. log format to generate a generally linear slope. In particular, the copy number and times for each standard control (in log format) are first plotted on a graph (see six data points in FIG. 6). Next, standard linear regression methods were used to determine the best fit for a slope between these data points (see FIG. 6). This slope is described by a slope equation that is determined based on the linear regression. In this example, the slope is described by the following slope equation: $y=11647 X^{-0.3453}$.

Next, it was determined where the threshold signal line intersects the experimental curves. In this example, it was determined that the threshold signal line intersects the three experimental curves at the time points shown in Table 3 below.

TABLE 3

| Sample ID | Time (sec) | Back calculated copies of miR-21 |
|---|---|---|
| B4 | 126.0 | 493,158 |
| E4 | 795.2 | 2,377 |
| F4 | 2367.2 | 101 |

Using the slope equation determined above ($y=11647 X^{-0.3453}$) and the intersecting time points presented in Table 3 as X in the equation, allowed a back calculation of the copies of miR-21 present in the experimental samples. The calculated amounts for each of the three experimental samples are presented in Table 3.

EXAMPLE 2

Target Sequence Quantification with Alternate Thresholds

This Example was run in a similar manner to Example 1. In this Example, all the data corresponds to known copy numbers for miR-21 (FAM) or U6 snRNA (ROX). FAM data correspond to miR-21 in duplicates for each level. The target levels (i.e., copy #) are as follows: 6,000,000; 1,200,000; 240,000; 48,000; 9,600; 1,920; 384; and 0. ROX data correspond to U6 and/or U24 snRNA in duplicates for each level and the target levels (i.e., copy #) are as follows: 36,000,000; 7,200,000; 1,440,000; 288,000; 57,600; 11,520; 2,304; and 0.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, mathematics, or related fields are intended to be within the scope of the following claims.

We claim:

1. A method of quantifying a target in an experimental sample comprising:
   a) measuring a nucleic acid detection assay signal at a plurality of time intervals from an experimental sample and at least two standard control samples containing known target copy numbers that are different, thereby generating signal data;
   b) providing said signal data to a computer system, wherein said computer system has stored therein a target quantifying software application;
   c) processing said signal data with said target quantifying software application such that said target quantifying software:
      i) generates a threshold signal line having i) an initial signal value at time zero, and ii) a threshold slope; wherein said threshold signal line is above background level and intersects said experimental curve and two or more of said at least two standard control curves;
      ii) processes said signal data and said threshold signal line to generate an experimental intersecting time value and at least two standard control intersecting time values;
      iii) processes said at least two standard control intersecting time values and said known target copy numbers to generate log plot data comprising coordinates for a log/log plot, or a linear/log plot, of said intersecting time values versus said known target copy numbers;
      iv) processes said log plot data to generate a slope equation describing a resulting slope fit to said log plot data; and
      v) processes said experimental intersecting time value with said slope equation to generate a quantified target copy number for said experimental sample; and
   d) transmitting said quantified target copy number to a user interface display.

2. The method of claim 1, wherein said threshold slope of is zero, or wherein said threshold slope is negative.

3. The method of claim 1, wherein said nucleic acid detection assay comprises an invasive cleavage assay.

4. The method of claim 1, wherein said nucleic acid detection assay is performed under isothermal conditions.

5. The method of claim 1, wherein said target comprises a nucleic acid sequence.

6. The method of claim 5, wherein said nucleic acid sequence comprises a micro-RNA or siRNA sequence.

7. A system for quantifying a target in an experimental sample comprising:
   a) a device configured to detect assay signal level at a plurality of time intervals from an experimental sample and at least two standard control samples containing known target copy numbers that are different, to generate initial signal data;
   b) a target quantifying software application configured to:
      i) process said initial signal data to generate signal data that is capable of being plotted as an experimental curve and at least two standard control curves;
      ii) generate a threshold signal line having i) an initial signal value at time zero, and ii) a threshold slope; wherein said threshold signal line is above background, and intersects said experimental curve and two or more of said at least two standard control curves;
      iii) process said signal data and said threshold signal line to generate an experimental intersecting time value and at least two standard control intersecting time values;
      iv) process said at least two standard control intersecting time values and said known target copy numbers to generate log plot data comprising coordinates for a log/log plot, or linear/log plot, of said intersecting time values versus said known target copy numbers;
      v) process said log plot data to generate a slope equation describing a resulting slope fit to said log plot data; and
      vi) process said experimental intersecting time value with said slope equation to generate a quantified target copy number for said experimental sample; and
   c) a computer system having stored therein said target quantifying software application, wherein said computer system comprises computer memory and a computer processor.

8. The system of claim 7, wherein said target comprises a nucleic acid sequence.

9. The system of claim 8, wherein said nucleic acid sequence comprises an RNA or DNA sequence.

10. The system of claim 7, wherein said assay signal level is generated by a nucleic acid detection assay.

11. The system of claim 10, wherein said nucleic acid detection assay comprises an invasive cleavage assay.

12. The system of claim 10, wherein said nucleic acid detection assay is configured to run under isothermal conditions.

* * * * *